(12) United States Patent
Tadross et al.

(10) Patent No.: US 12,059,292 B2
(45) Date of Patent: Aug. 13, 2024

(54) SYSTEMS AND METHODS FOR ULTRASOUND PROBE POSITIONING

(71) Applicant: GE Precision Healthcare LLC, Wauwatosa, WI (US)

(72) Inventors: Rimon Tadross, Milwaukee, WI (US); Michael J. Washburn, Wauwatosa, WI (US); Todd Schueneman, Pewaukee, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 17/649,538

(22) Filed: Jan. 31, 2022

(65) Prior Publication Data
US 2023/0240648 A1 Aug. 3, 2023

(51) Int. Cl.
*A61B 8/00* (2006.01)
*A61B 8/06* (2006.01)

(52) U.S. Cl.
CPC .............. *A61B 8/42* (2013.01); *A61B 8/06* (2013.01); *A61B 8/4444* (2013.01)

(58) Field of Classification Search
CPC ............ A61B 8/42; A61B 8/06; A61B 8/4444
See application file for complete search history.

(56) References Cited

U.S. PATENT DOCUMENTS

| 4,497,325 | A | * | 2/1985 | Wedel | A61M 5/3287 |
| | | | | | 604/116 |
| 7,857,763 | B2 | | 12/2010 | Tai | |
| 9,901,262 | B2 | | 2/2018 | Hammerling | |
| 10,813,620 | B2 | | 10/2020 | Owen et al. | |
| 2004/0015080 | A1 | | 1/2004 | Kelly et al. | |
| 2007/0055152 | A1 | | 3/2007 | Ukubo et al. | |
| 2008/0221519 | A1 | | 9/2008 | Schwach et al. | |
| 2010/0168577 | A1 | | 7/2010 | Vezina | |
| 2014/0180116 | A1 | * | 6/2014 | Lindekugel | A61B 8/4455 |
| | | | | | 600/459 |
| 2018/0153504 | A1 | | 6/2018 | Herickhoff et al. | |
| 2018/0263597 | A1 | | 9/2018 | Tchang et al. | |
| 2019/0277954 | A1 | * | 9/2019 | Bayarsaikhan | G01S 15/931 |
| 2020/0174118 | A1 | * | 6/2020 | Tadross | A61B 8/5223 |
| 2020/0174119 | A1 | | 6/2020 | Tadross et al. | |

FOREIGN PATENT DOCUMENTS

| WO | WO-0112068 A1 | * | 2/2001 | ............... A61B 8/08 |
| WO | WO-2018059947 A1 | * | 4/2018 | ............... A61B 8/04 |

* cited by examiner

*Primary Examiner* — Baisakhi Roy
*Assistant Examiner* — Kaitlyn E Sebastian
(74) *Attorney, Agent, or Firm* — McCoy Russell LLP

(57) ABSTRACT

Methods and systems are provided for ultrasound imaging, and in particular, for controlling a position of an ultrasound probe. In one example, a probe guide comprises a body shaped to receive an ultrasound probe and including a first detent shaped to maintain the ultrasound probe in a first rotational position along an axis of the body and a second detent shaped to maintain the ultrasound probe in a second rotational position along the axis of the body.

20 Claims, 12 Drawing Sheets

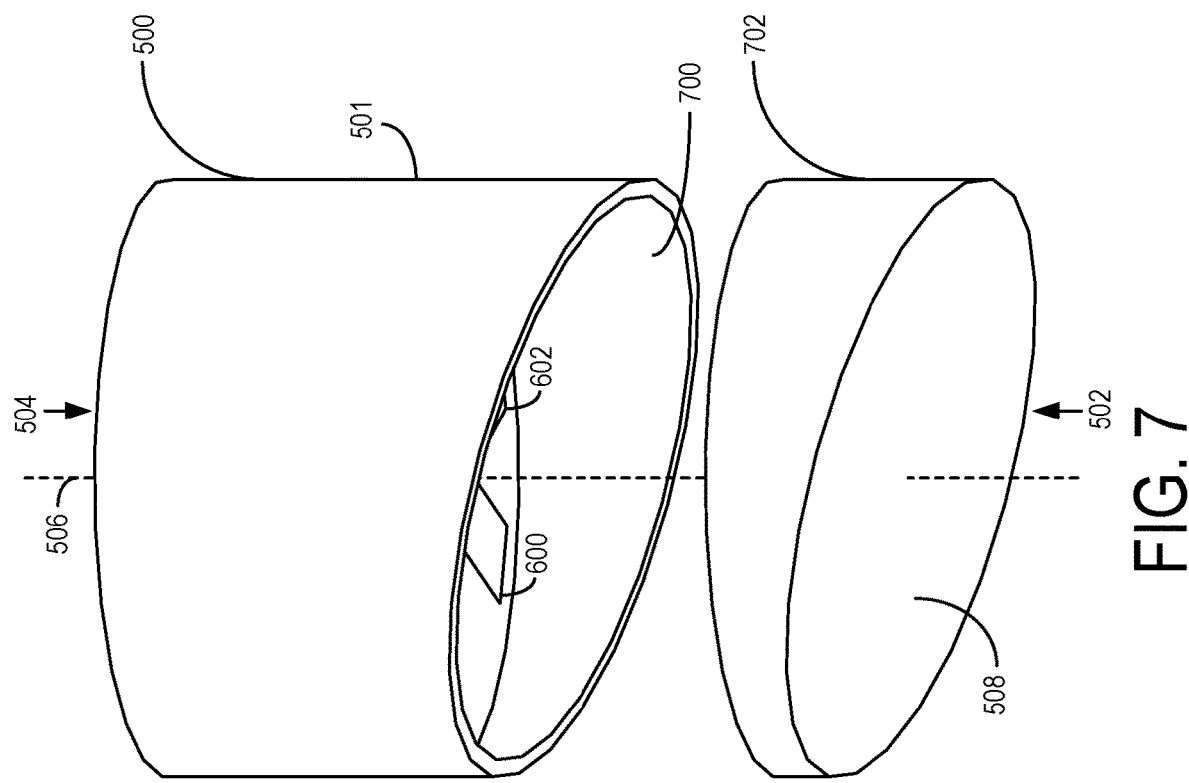

SYSTEMS AND METHODS FOR ULTRASOUND PROBE POSITIONING

FIELD

The present description relates generally to methods and systems for ultrasound imaging, and in particular, for controlling a position of an ultrasound probe.

BACKGROUND

Ultrasound imaging may be used to detect the presence of blood flow in the body. In some configurations, such as those disclosed by U.S. Publication No. 2020/0174118, pulse wave Doppler calculates the Doppler shift of ultrasound signals within a Doppler gate and uses the Doppler shift to estimate flow velocity by assuming that the vessel has a circular cross-section. In other configurations, average flow velocity, and cross sectional area at a given location in a vessel can be estimated via Color Flow and B-mode imaging using a probe that can be rotated around the depth axis using a probe guide. The average velocity and cross sectional area are then used to calculate the instantaneous volume flow rate of the blood flow. The volume flow rate may be calculated based on the images in combination with detailed position data of the ultrasound probe.

BRIEF DESCRIPTION

In one embodiment, a probe guide comprises: a body shaped to receive an ultrasound probe and including a first detent shaped to maintain the ultrasound probe in a first rotational position along an axis of the body and a second detent shaped to maintain the ultrasound probe in a second rotational position along the axis of the body.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIG. 7 shows an exploded bottom perspective view of the ultrasound probe guide of FIGS. 5-6.

FIGS. 5-18 and 20-22 are shown approximately to scale, although other relative dimensions may be used, if desired.

DETAILED DESCRIPTION

The following description relates to systems and methods for systems for ultrasound imaging, and in particular, for controlling a position of an ultrasound probe. An ultrasound imaging system, such as the ultrasound imaging system shown by FIG. 1, includes an ultrasound probe, such as the ultrasound probe shown by FIG. 2, and a probe guide, such as the probe guide shown by FIGS. 5-10 and the probe guide shown by FIGS. 11-18. The probe guide is shaped to receive the ultrasound probe, as shown by FIG. 3. A lower end of the probe guide may be angled in some embodiments, as shown by FIGS. 5-7 and 20-22, and in other embodiments the lower end may be flat and parallel with an upper end. During imaging of a subject via the ultrasound imaging system, the probe guide is arranged at an anatomy of interest of the subject, such as the vessel shown by FIG. 4, with the rotational position of the ultrasound probe controlled by the probe guide. The probe guide may maintain the rotational position of the ultrasound probe at any of a plurality of fixed rotational positions, with each rotational position defined by a corresponding detent of the probe guide. To determine a volume flow rate through the vessel, an image may be acquired by the ultrasound probe for each of the fixed rotational positions defined by the probe guide and the volume flow rate may be calculated based on the set of images. In some embodiments, for each rotational position, the ultrasound probe may seat directly against a corresponding detent of the probe guide, and for other embodiments, the ultrasound probe may rotate within the probe guide to each of the rotational positions and may lock to each rotational position via a corresponding detent of the probe guide. By maintaining the rotational position of the ultrasound probe via the probe guide, the probe guide may increase a precision of acquisition of images along predetermined imaging planes, which may increase an accuracy of the calculation of the volume flow rate.

Figure 1:
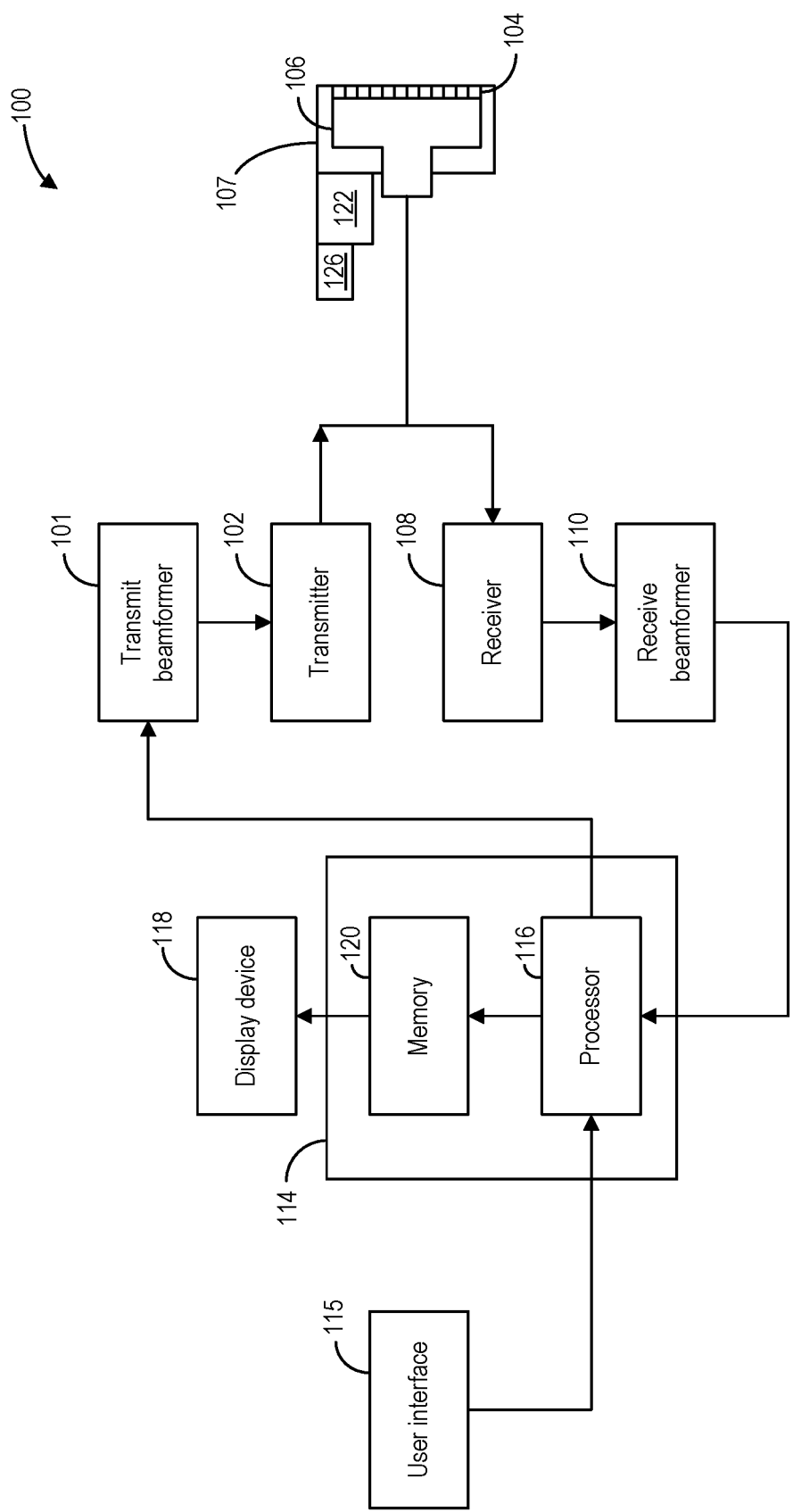
FIG. 1 schematically shows an ultrasound system according to an embodiment.

FIG. 1 is a schematic diagram of an ultrasound imaging system 100. The ultrasound imaging system 100 includes a transmit beamformer 101 and a transmitter 102 that drive elements 104 within an ultrasound probe 106 to emit pulsed ultrasonic signals into an imaged subject's body (not shown). The ultrasound probe 106 may, for instance, be a linear array probe, a curvilinear array probe, a sector probe, or any other type of ultrasound probe configured to acquire both 2D B-mode data and 2D colorflow (CF) data or both 2D B-mode data and another ultrasound mode that detects blood flow velocity in the direction of a vessel axis. The ultrasound probe 106 may have the elements 104 arranged in a 1D array. Pulsed ultrasonic signals may be back-scattered from structures in the body, like blood cells or muscular tissue, to produce echoes that return to the elements 104. The echoes are converted into electrical signals, or ultrasound data, by the elements 104, and the electrical signals are received by a receiver 108. The electrical signals representing the received echoes are passed through a receive beamformer 110 that outputs ultrasound data. According to some embodiments, the ultrasound probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the ultrasound probe 106. The terms "scan" or "scanning" may also be used in this disclosure to refer to acquiring data through the process of transmitting and receiving ultrasonic signals. The terms "data" and "ultrasound data" may be used in this disclosure to refer to either one or more datasets acquired with an ultrasound imaging system.

The ultrasound imaging system 100 may include an input device 115. The input device 115 may be used to control the input of patient data or to select various modes, operations, and parameters, and the like. The input device 115 may include one or more of a keyboard, a dedicated hard key, a touch pad, a mouse, a track ball, a rotary control, a slider, and the like. The input device 115 may include a proximity sensor configured to detect objects or gestures that are within several centimeters of the proximity sensor. The input device 115 may include a touch screen that is positioned in front of the display device 118 or the touch screen may be separate from the display device 118. The input device 115 (which may be referred to herein as a user interface) may also include one or more physical controls (such as buttons, sliders, rotary knobs, keyboards, mice, trackballs, etc.) either alone or in combination with graphical user interface icons displayed on the display screen. According to some embodiments, the input device 115 may include a combination of physical controls (such as buttons, sliders, rotary knobs, keyboards, mice, trackballs, etc.) and user interface icons displayed on either the display device 118 or on a touch sensitive display screen.

The display device 118 may be configured to display a graphical user interface (GUI) from instructions stored in a memory 120. The GUI may include user interface icons to represent commands and instructions. The user interface icons of the GUI are configured so that a user may select commands associated with each specific user interface icon in order to initiate various functions controlled by the GUI. For example, various user interface icons may be used to represent windows, menus, buttons, cursors, scroll bars, etc. According to embodiments where the input device 115 includes a touch screen, the touchscreen may be configured to interact with the GUI displayed on the display device 118. The touch screen may be a single-touch touch screen that is configured to detect a single contact point at a time or the touch screen may be a multi-touch touch screen that is configured to detect multiple points of contact at a time. For embodiments where the touch screen is a multi-point touch screen, the touch screen may be configured to detect multi-touch gestures involving contact from two or more of a user's fingers at a time. The touch screen may be a resistive touch screen, a capacitive touch screen, or any other type of touch screen that is configured to receive inputs from a stylus or one or more of a user's fingers. According to other embodiments, the touchscreen may be an optical touch screen that uses technology such as infrared light or other frequencies of light to detect one or more points of contact initiated by a user.

According to various embodiments, the input device 115 may include an off-the-shelf consumer electronic device such as a smartphone, a tablet, a laptop, etc. For purposes of this disclosure, the term "off-the-shelf consumer electronic device" is defined to be an electronic device that was designed and developed for general consumer use and one that was not specifically designed for use in a medical environment. According to some embodiments, the consumer electronic device may be physically separate from the rest of the ultrasound imaging system. The consumer electronic device may communicate with an electronic controller 114 including a processor 116 through a wireless protocol, such Wi-Fi, Bluetooth, Wireless Local Area Network (WLAN), near-field communication, etc. According to an embodiment, the consumer electronic device may communicate with the processor 116 through an open Application Programming Interface (API).

The ultrasound imaging system 100 also includes the processor 116 to control the transmit beamformer 101, the transmitter 102, the receiver 108, and the receive beamformer 110. The processor 116 is configured to receive inputs from the input device 115. The receive beamformer 110 may be either a conventional hardware beamformer or a software beamformer according to various embodiments. If the receive beamformer 110 is a software beamformer, it may comprise one or more of the following components: a graphics processing unit (GPU), a microprocessor, a central processing unit (CPU), a digital signal processor (DSP), or any other type of processor capable of performing logical operations. The receive beamformer 110 may be configured to perform conventional beamforming techniques as well as techniques such as retrospective transmit beamforming (RTB). If the receive beamformer 110 is a software beamformer, the processor 116 may be configured to perform some or all of the functions associated with the receive beamformer 110.

The processor 116 is in electronic communication with the ultrasound probe 106. The processor 116 may control the ultrasound probe 106 to acquire ultrasound data. The processor 116 controls which of the elements 104 are active and the shape of a beam emitted from the ultrasound probe 106. The processor 116 is also in electronic communication with the display device 118, and the processor 116 may process the ultrasound data into images for display on the display device 118. The processor 116 may be configured to display one or more non-image elements on the display device 118. The instructions for displaying each of the one or more non-image elements may be stored in the memory 120. For purposes of this disclosure, the term "electronic communication" may be defined to include both wired and wireless connections. The processor 116 may include a central processing unit (CPU) according to an embodiment.

According to other embodiments, the processor 116 may include other electronic components capable of carrying out processing functions, such as a digital signal processor, a field-programmable gate array (FPGA), a graphics processing unit (GPU), or any other type of processor. According to other embodiments, the processor 116 may include multiple electronic components capable of carrying out processing functions. For example, the processor 116 may include two or more electronic components selected from a list of electronic components including: a central processing unit (CPU), a digital signal processor (DSP), a field-programmable gate array (FPGA), and a graphics processing unit (GPU). According to another embodiment, the processor 116 may also include a complex demodulator (not shown) that demodulates the RF data and generates raw data. In another embodiment the demodulation may be carried out earlier in the processing chain. The processor 116 may be adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. Real-time frame rates may vary based on the specific parameters used during the acquisition. The data may be stored temporarily in a buffer during a scanning session and processed in less than real-time. Some embodiments may include multiple processors (not shown) to handle the processing tasks. For example, an embodiment may use a first processor to demodulate and decimate the RF signal and a second processor to further process the data prior to displaying an image. It should be appreciated that other embodiments may use a different arrangement of processors. For embodiments where the receive beamformer 110 is a software beamformer, the processing functions attributed to the processor 116 and the software beamformer hereinabove may be performed by a single processor, such as the receive beamformer 110 or the processor 116. In some embodiments the processing functions attributed to the processor 116 and the software beamformer may be allocated in a different manner between any number of separate processing components.

According to an embodiment, the ultrasound imaging system 100 may continuously acquire real-time ultrasound data at a frame-rate of, for example, 10 Hz to 30 Hz. A live, or real-time, image may be generated based on the real-time ultrasound data. Other embodiments may acquire data and or display the live image at different frame-rates. For example, some embodiments may acquire real-time ultrasound data at a frame-rate of less than 10 Hz or greater than 30 Hz depending on the size of the ultrasound data and the intended application. Other embodiments may use ultrasound data that is not real-time ultrasound data. The memory 120 is included for storing processed frames of acquired data and instructions for displaying one or more non-image elements on the display device 118. In an exemplary embodiment, the memory 120 is of sufficient capacity to store image frames of ultrasound data acquired over a period of time at least several seconds in length. The memory 120 may comprise any known data storage medium. The memory or storage device may be a component of the ultrasound imaging system 100, or the memory or storage device may external to the ultrasound imaging system 100.

Optionally, embodiments may be implemented utilizing contrast agents and contrast imaging. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component, and generating an ultrasound image by utilizing the enhanced harmonic component. Separation of harmonic components from the received signals is performed using suitable filters.

In various embodiments, data may be processed by other or different mode-related modules by the processor 116 (e.g., B-mode, Color Doppler, M-mode, Color M-mode, spectral Doppler, Elastography, tissue velocity imaging (TVI), strain, strain rate and combinations thereof, and the like) to form images or data. For example, one or more modules may generate B-mode, color Doppler, M-mode, color M-mode, spectral Doppler, Elastography, TVI, strain, strain rate and combinations thereof, and the like. The image beams and/or frames are stored and timing information indicating a time at which the data was acquired in memory may be recorded. The modules may include, for example, a scan conversion module to perform scan conversion operations to convert the image frames from beam space coordinates to display space coordinates. A video processor module may be provided that reads the image frames from a memory and displays the image frames in real time while a procedure is being carried out on a patient. A video processor module may store the image frames in an image memory, from which the images are read and displayed.

Ultrasound imaging system 100 includes a probe guide 107. Probe guide 107 is configured to maintain a rotational position of the ultrasound probe 106 during imaging of a subject (e.g., a patient), similar to the examples described further below. In some embodiments, the probe guide 107 may include a position sensing system 122. The position sensing system 122 may include one or more sensors, such as sensor 126, configured to detect the rotational position of the ultrasound probe 106 during conditions in which the ultrasound probe 106 is coupled with the probe guide 107. For example, during conditions in which the ultrasound probe 106 is maintained in a first rotational position by the probe guide 107, the sensor 126 may sense the position of the ultrasound probe 106 and transmit data indicating the position of the ultrasound probe 106 to the controller 114 (e.g., to processor 116). During conditions in which the position of the ultrasound probe 106 is adjusted from the first rotational position to a second rotational position, the one or more sensors of the position sensing system 122 may detect the rotational position of the ultrasound probe 106 throughout the transition. According to an embodiment, the sensor 126 may be an electromagnetic position sensor, optical position sensor, or mechanical position sensor. The position sensing system 122 may be configured to detect the position of the ultrasound probe 106 in real-time.

Figure 2:
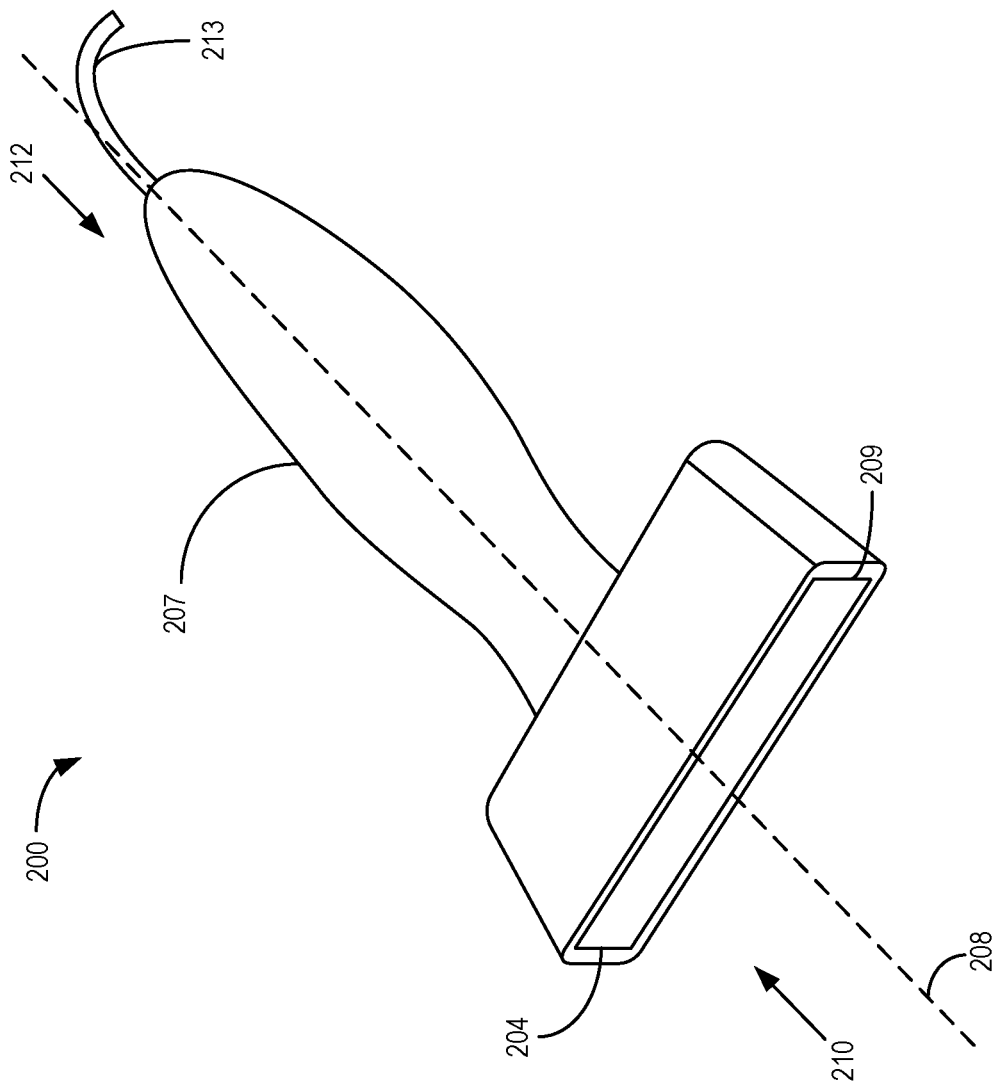
FIG. 2 shows an ultrasound probe according to an embodiment.
Figure 3:
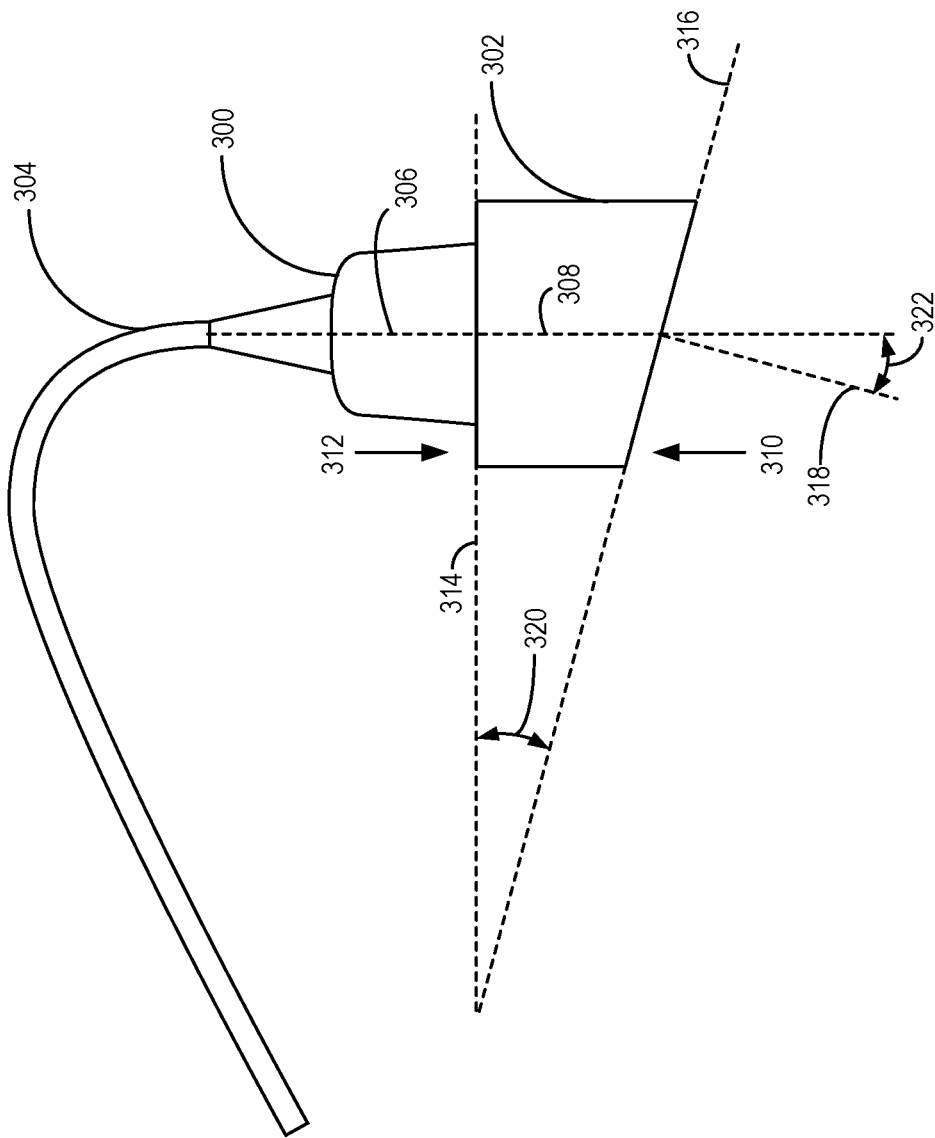
FIG. 3 shows an ultrasound probe coupled with an ultrasound probe guide according to an embodiment, where the ultrasound probe may have an angled lower surface.

FIG. 2 is a schematic perspective view of an ultrasound probe 200 in accordance with an embodiment. The ultrasound probe 200 may be similar to, or the same as, the ultrasound probe 106 described above with reference to FIG. 1. The ultrasound probe 200 shown in FIG. 2 is a linear probe. Elements 204 (which may be similar to, or the same as, elements 104 described above with reference to FIG. 1) are arranged in a linear array. The ultrasound probe 200 may have a different configuration according to various embodiments. For example, the ultrasound probe 200 may be a curved array probe or a linear array probe. A central axis 208 of the ultrasound probe 200 is shown by FIG. 2. The central axis 208 extends through and is parallel to, a handle 207 of the ultrasound probe 200. According to the embodiment shown in FIG. 2, central axis 208 of the ultrasound probe 200 is perpendicular to an array face 209 (which may be referred to herein as an end surface) with the elements 204. The array face 209 and elements 204 are positioned at a first end 210 of the ultrasound probe 200 and opposite to the handle 207 arranged at a second end 212 of the ultrasound probe 200. In some examples, the ultrasound probe 200 may be configured to communicate wirelessly with an electronic controller of an ultrasound imaging system (e.g., electronic controller 114 described above with reference to FIG. 1). In other examples the ultrasound probe 200 may be configured with a cable, such as cable 213, and may communicate electronically with the controller via the cable 213.

Referring to FIG. 3, a side view of an ultrasound probe 300 coupled with an ultrasound probe guide 302 is shown according to an embodiment. The ultrasound probe may be similar to, or the same as, the ultrasound probe 200 shown by FIG. 2 and described above and/or the ultrasound probe 106 shown by FIG. 1 and described above. The probe guide 302 may be similar to, or the same as, the probe guide 107 shown by FIG. 1 and described above.

The ultrasound probe 300 may communicate electronically with an electronic controller (e.g., similar to, or the same as, the electronic controller 114 described above with reference to FIG. 1) via cable 304. In some embodiments, the ultrasound probe 300 may communicate wirelessly (e.g., via Wi-Fi) with the electronic controller.

As shown, during conditions in which the ultrasound probe 300 is coupled with the probe guide 302 (e.g., seated within the probe guide 302), a central axis 306 of the ultrasound probe 300 is aligned coaxially with a central axis 308 of the probe guide 302. The ultrasound probe 300 may be adjusted to different rotational positions around the central axis 308 of the probe guide 302 while maintaining the central axis 306 of the ultrasound probe 300 in the coaxial alignment with the central axis 308 of the probe guide 302. Elements of the ultrasound probe 300 configured to emit pulsed ultrasonic signals (e.g., similar to, or the same as, elements 104 described above with reference to FIG. 1) are arranged toward a first end 310 of the probe guide 302 during conditions in which the ultrasound probe 300 is coupled with the probe guide 302. During imaging of a subject (e.g., a patient), the first end 310 of the probe guide 302 may be positioned directly in contact with the body of the subject at the location of an anatomy of interest of the subject (e.g., a blood vessel), with the first end 310 arranged closer to the body than an opposing second end 312 of the probe guide 302. In particular, the first end 310 of the probe guide 302 may be positioned in direct contact with the body of the subject, with the elements of the ultrasound probe 300 arranged at the first end 310 such that the elements may emit pulsed ultrasonic signals directly to the body of the subject. The ultrasound probe 300 may be coupled to the probe guide 302 by inserting the ultrasound probe 300 through the second end 312 of the probe guide 302 in some embodiments.

In the embodiment shown, the first end 310 of the probe guide 302 is angled relative to the second end 312 of the probe guide 302. For example, axis 314 shown parallel with the second end 312 is angled relative to axis 316 shown parallel with the first end 310 by angle 320. The axis 314 is arranged perpendicular to the central axis 308 of the probe guide 302. In some embodiments, the angle 320 may be approximately 15 degrees. By angling the first end 310 of the probe guide 302 as shown, an ease of positioning of the probe guide 302 and the ultrasound probe 300 relative to the subject to be imaged may be increased. In particular, with the angled configuration of the first end 310 of the probe guide 302, during conditions in which the probe guide 302 is positioned against the subject, the central axis 308 of the probe guide 302 is arranged at an angle 322 relative to an axis 318 normal to the subject at the location of contact between the probe guide 302 and the subject. As a result, the ultrasound probe 300 may be more easily oriented toward a desired imaging plane while the ultrasound probe 300 is coupled to the probe guide 302. The angled configuration of the first end 310 relative to the second end 312 may enable the probe guide 302 to be positioned against the body of the imaged subject without using a "heel toe" probe positioning technique, which may increase an ease of maintaining the position of the vessel throughout imaging. Additionally, the angled configuration may lower the Doppler angle for an oblique imaging plane (e.g., second imaging plane 406 described below with reference to FIG. 4), which may increase an ease of imaging of the subject.

The position of the probe guide 302 relative to the imaged subject may be fixed (e.g., maintained) by straps or other fastening mechanisms. For example, during imaging of a vessel of the subject, such as the femoral artery, the probe guide 302 may be positioned directly in contact with the body of the subject at the location of the vessel to be imaged and may be maintained in the desired location via one or more straps or other fastening devices. The straps or other fastening mechanisms may be used with each of the probe guide embodiments described herein to maintain the position of the probe guide relative to the imaged subject (e.g., during imaging of the subject for diagnosis or evaluation, such as for peripheral vascular disease diagnosis). As one example, the one or more straps or other fastening devices may extend around (e.g., wrap around) a limb of the imaged subject and couple with the probe guide in order to maintain the probe guide in direct contact with the body of the subject.

Figure 4:
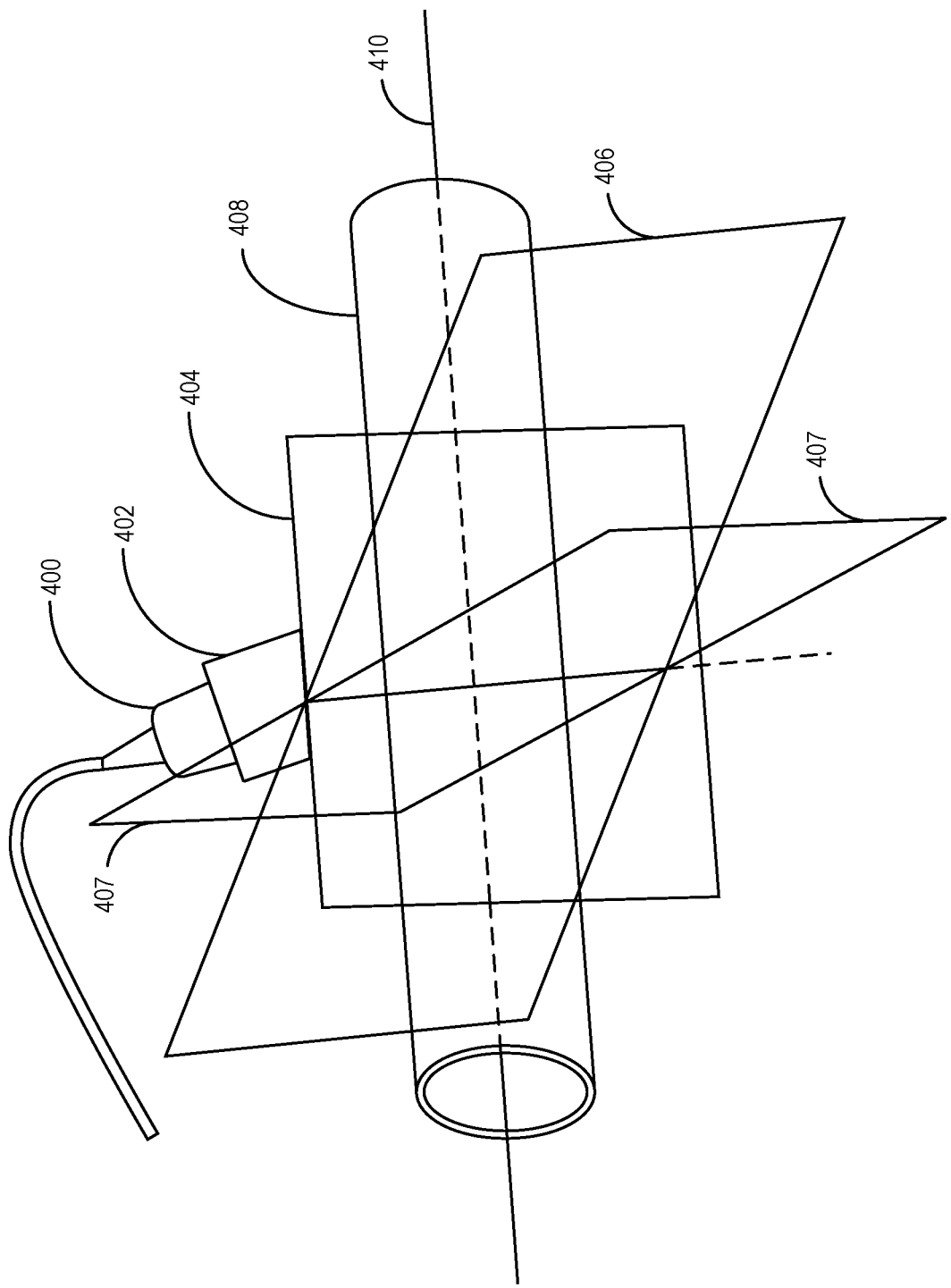
FIG. 4 schematically shows an ultrasound probe, an ultrasound probe guide, a first imaging plane, a second imaging plane, a third imaging plane, and a vessel according to an embodiment.

Referring to FIG. 4, an ultrasound probe 400, an ultrasound probe guide 402, a first imaging plane 404, a second imaging plane 406, a third imaging plane 407, and a vessel 408 are schematically shown according to an embodiment. The ultrasound probe 400 may be similar to, or the same as, the ultrasound probe 300 shown by FIG. 3 and described above, the ultrasound probe 200 shown by FIG. 2 and described above, and/or the ultrasound probe 106 shown by FIG. 1 and described above. The probe guide 402 may be similar to, or the same as, the probe guide 302 shown by FIG. 3 and described above and/or the probe guide 107 shown by FIG. 1 and described above.

The first imaging plane 404 extends along longitudinal axis 410 of vessel 408, the second imaging plane 406 is oblique (e.g., angled) relative to the longitudinal axis 410 and the first imaging plane 404, and third imaging plane 407 is arranged orthogonal to the first imaging plane 404 and longitudinal axis 410.

An operator of the ultrasound imaging system (e.g., a clinician) may acquire a first image of the vessel 408 with the ultrasound probe 400 oriented to the first imaging plane 404 while the probe guide 402 maintains the rotational position of the ultrasound probe 400 relative to the vessel 408 and the probe guide 402. In particular, the probe guide 402 may maintain the rotational position of the ultrasound probe 400 such that the ultrasound probe 400 does not move from alignment with the first imaging plane 404 and longitudinal axis 410 during acquisition of the first image. The operator may then adjust the rotational position of the ultrasound probe 400 via the probe guide 402 prior to acquisition of a second image, where the second image is acquired while the ultrasound probe 400 is oriented to the second imaging plane 406. The rotational position of the ultrasound probe 400 may be maintained by the probe guide 402 with the ultrasound probe 400 oriented to the second imaging plane 406 throughout acquisition of the second image. In some embodiments (e.g., as described below with reference to FIGS. 5-10), the operator may decouple the ultrasound probe 400 from the probe guide 402 following acquisition of the first image and re-couple the ultrasound probe 400 with the probe guide 402 in alignment with the second imaging plane prior to acquisition of the second image. In other embodiments (e.g., as described below with reference to FIGS. 11-18), the operator may rotate the ultrasound probe 400 from alignment with the first imaging plane to alignment with the second imaging plane without decoupling the ultrasound probe 400 from the probe guide 402. In each example, throughout acquisition of the first image and the second image and throughout the transition of the rotational position of the ultrasound probe 400, the position of the probe guide 402 is maintained relative to the vessel 408. Further, throughout acquisition of the first image and the second image, a central axis of the ultrasound probe 400 (e.g., central axis 306 shown by FIG. 3 and described above) is maintained coaxial with a central axis of the probe guide 402 (e.g., central axis 308 shown by FIG. 3 and described above). In embodiments in which the probe guide 402 includes a position sensing system including one or more position sensors (e.g., similar to position sensing system 122 including sensor 126 described above with reference to FIG. 1), the probe guide 402 may transmit position information of the ultrasound probe 400 to the controller (e.g., controller 114 described above with reference to FIG. 1) while the ultrasound probe 400 is coupled with the probe guide 402. Following acquisition of the second image, the operator may adjust the rotational position of the ultrasound probe 400 via the probe guide 402 to orient the ultrasound probe 400 to the third imaging plane 407, and a third image may be acquired while the ultrasound probe 400 is oriented to the third imaging plane 407. The rotational position of the ultrasound probe 400 may be maintained by the probe guide 402 with the ultrasound probe 400 oriented to the third imaging plane 407 throughout acquisition of the third image.

The controller may determine (e.g., calculate) the volume flow rate through the vessel 408 based on each of the first image, the second image, and the third image. Because the position of the ultrasound probe 400 relative to the probe guide 402 during conditions in which the ultrasound probe 400 is coupled to the probe guide 402 is controlled by engagement of a corresponding detent of the probe guide 402, the controller may determine the volume flow rate with a reduced amount of information relative to systems in which the position of the ultrasound probe 400 is tracked (e.g., monitored) throughout the scan of the vessel 408. For example, the ultrasound probe 400 may be coupled to the probe guide 402 with a first detent of the probe guide 402 in an engaged condition (e.g., similar to the examples described further below), with the first detent maintaining the position of the ultrasound probe 400 relative to the probe guide 402. The probe guide 402 is configured such that each detent of the probe guide 402 corresponds to a fixed rotational position of the ultrasound probe 400 during conditions in which the ultrasound probe 400 is coupled with the probe guide 402 (e.g., while the ultrasound probe 400 is coupled with the probe guide 402, engagement of a first detent maintains (e.g., locks) the ultrasound probe 400 in a first rotational position relative to the probe guide 402, engagement of a second detent maintains (e.g., locks) the ultrasound probe in a second rotational position relative to the probe guide 402, and engagement of a third detent maintains (e.g., locks) the ultrasound probe in a third rotational position relative to the probe guide 402).

For each detent of the probe guide 402, the corresponding rotational position of the ultrasound probe 400 while the ultrasound probe 400 is coupled with the probe guide 402 may be known by the controller (e.g., stored in non-transitory memory of the controller). As one example, engagement of the first detent of the probe guide 402 may result in an initial rotational position of the ultrasound probe 400 relative to the probe guide 402 (e.g., 0 degrees around a central axis of the probe guide 402), engagement of the second detent of the probe guide 402 may result in a rotational position of the ultrasound probe 400 offset from the initial position around the central axis by a first amount (e.g., 45 degrees), and engagement of the third detent of the probe guide 402 may result in a rotational position of the ultrasound probe 400 offset from the initial position around the central axis by a second amount (e.g., 90 degrees).

The probe guide 402 may include one or more sensors configured to sense engagement of the detents of the probe guide 402, and the controller may determine the position of the ultrasound probe 400 based on the engagement of the detents. For example, during conditions in which the controller determines that the first detent is engaged, the controller may determine that the ultrasound probe 400 is in the first rotational position, and during conditions in which the controller determines that the second detent is engaged, the controller may determine that the ultrasound probe 400 is in the second rotational position, etc.

In some examples, the probe guide 402 may not include the sensors described above. In such examples, the controller may determine the relative position of the ultrasound probe 400 for each image in a sequence of images acquired by the ultrasound probe 400 based on an acquisition timing of each image. For example, the ultrasound probe 400 may acquire a first image, a second image, and a third image of the vessel 408 in a single scan of the vessel 408, with the first image acquired before the second image with no other images acquired therebetween, and with the second image acquired before the third image with no other images acquired therebetween. The controller may determine based on the sequence in which the images are acquired that the position of the ultrasound probe 400 during acquisition of the first image corresponds to the initial rotational position (which may be referred to herein as the first rotational position) of the ultrasound probe 400 (e.g., the rotational position the ultrasound probe 400 is maintained in by engagement of the first detent). The controller may further determine based on the sequence that the position of the ultrasound probe 400 during acquisition of the second image corresponds to the second rotational position of the ultrasound probe 400 (e.g., the rotational position the ultrasound probe 400 is maintained in by engagement of the second detent, where the second rotational position is offset from the initial rotational position around the central axis of the probe guide 402). The controller may further determine based on the sequence that the position of the ultrasound probe 400 during acquisition of the third image corresponds to the third rotational position of the ultrasound probe 400 (e.g., the rotational position the ultrasound probe 400 is maintained in by engagement of the third detent, where the third rotational position is offset from the initial rotational position and the second rotational position around the central axis of the probe guide 402). In this way, the controller may determine the position of the ultrasound probe 400 during acquisition of each image without position information transmitted to the controller by sensors of the probe guide 402 and/or ultrasound probe 400. As a result, the ultrasound probe 400 and/or probe guide 402 may be configured without position sensors, which may reduce a cost, assembly time, and/or weight of the ultrasound imaging system.

The controller determines the volume flow rate through the vessel 408 based on the first image, the second image, and the third image. The volume flow rate may be defined by the equation:

Volume Flow Rate=Average Velocity*Vessel Cross Sectional Area where the Volume Flow Rate is the instantaneous volume flow rate of fluid through the vessel; the Average Velocity is the instantaneous spatially-averaged velocity within the vessel's cross section; and the Vessel Cross Sectional Area is the cross sectional area of the vessel normal to the longitudinal axis.

The average flow velocity may be defined by the equation:

$$\text{Average Velocity} = \frac{\sum_{i=0}^{N(\text{Vessel CF pixels in image 2})} Vel(i) * \alpha(i)}{\text{Cos(Doppler angle image 2)} * \sum_{i=0}^{N(\text{Vessel CF pixels in image 2})} \alpha(i)}$$

Where N (Vessel CF pixels in image 2) is the number of colorflow pixels in the second image; Vel(i) is the velocity of the ith colorflow pixel; $\alpha(i)$ is a weighting coefficient for the ith colorflow pixel, and Doppler angle image 2 is the angle between colorflow beams and the longitudinal axis of the vessel. The weighting coefficient $\alpha(i)$ may be set to 1 or may be calculated based on the power of the colorflow at the ith pixel.

The vessel cross sectional area may be defined by the equation:

Vessel Cross Sectional Area=Pixels Area(Image3)
*Cos(Area Angle Image3)

where Pixels Area (Image 3) is the measured area of the vessel's pixels in the third image, and the Area Angle Image 3 is the angle between the normal vector to the third plane (and the third image) and the longitudinal axis.

It should be appreciated that in other embodiments the controller may use different equations to calculate the volume flow rate based on the first image, the second image, the third image. Additionally, according to other embodiments, the controller may separate the processing operations for calculating the volume flow rate into a plurality of separate steps. According to an embodiment using the third image along the third plane, the area angle is defined to be the angle between a normal vector to the third plane and the longitudinal axis of the vessel and the pixel area would be calculated from the third, or transverse, image. The vessel color flow (CF) pixels, on the other hand, would be determined from the second, or oblique, image. The controller may display the volume flow rate on a display device (e.g., display device 118 shown by FIG. 1 and described above).

In some embodiments, the volume flow through the vessel 408 may be calculated as described below. In particular, the volume flow calculation may be performed while controlling the rotational position of the probe via the probe guide as described herein. For example, the volume flow calculation may be performed with the probe seated within various detents of the probe guide, as in the example shown by FIGS. 8-10. In the example, the probe acquires a first image while seated in the first detent, a second image while seated in the second detent, and a third image while seated in the third detent. As another example, the volume flow calculation may be performed with the probe guide seated within a central detent and with the probe guide being rotated to three different rotational positions while seated within the central detent, as in the example shown by FIGS. 16-18. In the example, the probe guide acquires a first image while in a first rotational position corresponding with engagement of a protrusion with a first detent, a second image while in a second rotational position corresponding with engagement of the protrusion with a second detent, and a third image while in a third rotational position corresponding with engagement of the protrusion with a third detent. In each example, the volume flow calculation uses each of the first image, the second image, and the third image together to determine the volume flow through the vessel 408.

A coordinate space for the position of the probe within the probe guide may be defined with an x-axis in a lateral direction of the probe and with a z-axis in a depth direction of the probe. The coordinate space is defined by the x-axis (lateral direction) of the probe and z-axis (depth direction) of the probe while the probe is in the longitudinal view position (e.g., the position in which the sensors of the probe are aligned with the longitudinal axis 410). Θ (theta) may be defined as an angle between the vessel 408 and the X-axis, ξ (zeta) may be defined as a steering angle between the ultrasound beam and the Z-axis, φ (phi) may be defined as the probe rotation angle, V may be defined as the unit vector in the vessel axis direction in the coordinate space (e.g., the direction of longitudinal axis 410), and U may be defined as the unit vector in the ultrasound beam in the coordinate space.

During conditions in which the probe is seated within the probe guide and positioned along the longitudinal axis of the vessel 408, the vectors V, and U may be defined in x, y, and z coordinates with V=(cos Θ, 0, sin Θ) and U=(sin ξ, cos ξ).

During conditions in which the probe is rotated to the oblique plane (e.g., the second imaging plane 406) and the probe guide is maintained against the body of the subject (where the probe guide determines the coordinate space), the vectors U and V become U' and V', respectively. V' may be defined as V'=V (remains the same due to the vessel 408 being in the same position relative to the probe guide as compared to the initial position in which the probe guide is positioned in alignment with the longitudinal axis, e.g., along first imaging plane 404), and U' may be defined as $U' = \begin{pmatrix} \cos\varphi & -\sin\varphi & 0 \\ \sin\varphi & \cos\varphi & 0 \\ 0 & 0 & 1 \end{pmatrix} U = \begin{pmatrix} \cos\varphi & -\sin\varphi & 0 \\ \sin\varphi & \cos\varphi & 0 \\ 0 & 0 & 1 \end{pmatrix} \begin{pmatrix} \sin\xi \\ 0 \\ \cos\xi \end{pmatrix} = \begin{pmatrix} \cos\varphi\sin\xi \\ \sin\varphi\sin\xi \\ \cos\xi \end{pmatrix}$ A parameter DopplerAngle may be the angle between the vessel axis direction V' and the colorflow ultrasound beam direction in the oblique imaging position U'. The DopplerAngle may be defined by DopplerAngle=$\cos^{-1}$(U', V'). For each color flow frame, the average velocity of the pixels of the frame may be calculated and then divided by the Cos(DopplerAngle) to get the actual angle-corrected value of the mean flow velocity for that colorflow frame for the vessel 408. This value is the instantaneous spatially averaged (across the cross section of the vessel 408) flow velocity of the blood in the vessel 408 at the measurement location. This instantaneous average velocity may then be multiplied by the vessel 408 cross-sectional area calculated from the image with the probe at the transverse location of the probe guide. The result is the instantaneous volumetric flow rate of the blood in the vessel 408 at the measured location.

Figure 5:
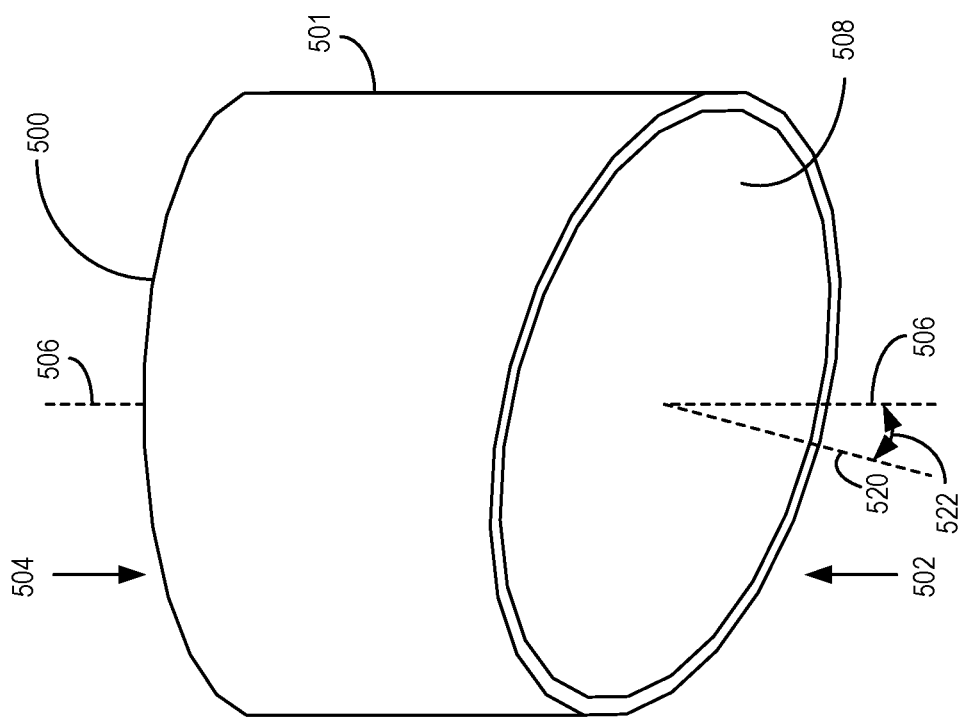
FIG. 5 shows a bottom perspective view of an ultrasound probe guide according to an embodiment.

Referring to FIG. 5, a bottom perspective view of an ultrasound probe guide 500 is shown according to an embodiment. The ultrasound probe guide 500 may be similar to, or the same as, the probe guide 402 shown by FIG. 4 and described above, the probe guide 302 shown by FIG. 3 and described above, and/or the probe guide 107 shown by FIG. 1 and described above. A body 501 of the probe guide 500 may receive an ultrasound probe, such as the ultrasound probe 400 shown by FIG. 4 and described above, and may maintain the rotational position of the ultrasound probe relative to the probe guide 500.

The probe guide 500 includes a first end 502 and a second end 504. During conditions in which the ultrasound probe is coupled with the probe guide 500, the elements of the ultrasound probe configured to emit pulsed ultrasonic signals (e.g., similar to elements 104 described above with reference to FIG. 1) are arranged closer to the first end 502 than the second end 504. The probe guide 500 shown by FIGS. 5-10 includes a lower end surface 508. In some examples the lower end surface 508 may be formed from a flexible material (e.g., silicone) configured to transmit ultrasonic pulses generated by the elements of the ultrasound probe to the imaged subject (e.g., a patient). In some examples, a portion of the ultrasound probe (e.g., the end portion including the elements configured to emit pulsed ultrasonic signals) may be flush with the lower end surface 508 or may protrude outward from an opening of the lower end surface 508 at the first end 502 of the probe guide 500.

The lower end surface 508 may be angled relative to an upper end surface 603 (shown by FIG. 6), similar to the example described above with reference to FIG. 4. In particular, the upper end surface 603 may extend radially relative to the central axis 506, and the lower end surface 508 may extend at an angle relative to the central axis 506 (e.g., axis 520 normal to the lower end surface 508 may be angled relative to central axis 506 by angle 522). In the configuration in which the lower end surface 508 is angled, the central axis 506 of the probe guide 500 may be angled by angle 522 relative to axis 520, where axis 520 is normal to the lower end surface 508 in direct contact with the subject during imaging of the subject. The angle 522 may be approximately 15 degrees, in some embodiments. While the ultrasound probe is coupled with the probe guide 500, a central axis of the ultrasound probe may be arranged coaxially with a central axis 506 of the probe guide 500. Although the probe guide 500 is shown including the angled lower end surface 508, in other embodiments the lower end surface may be parallel with the upper end surface 603 (e.g., the lower end surface 508 and upper end surface 603 may each extend radially relative to the central axis 506).

Figure 6:
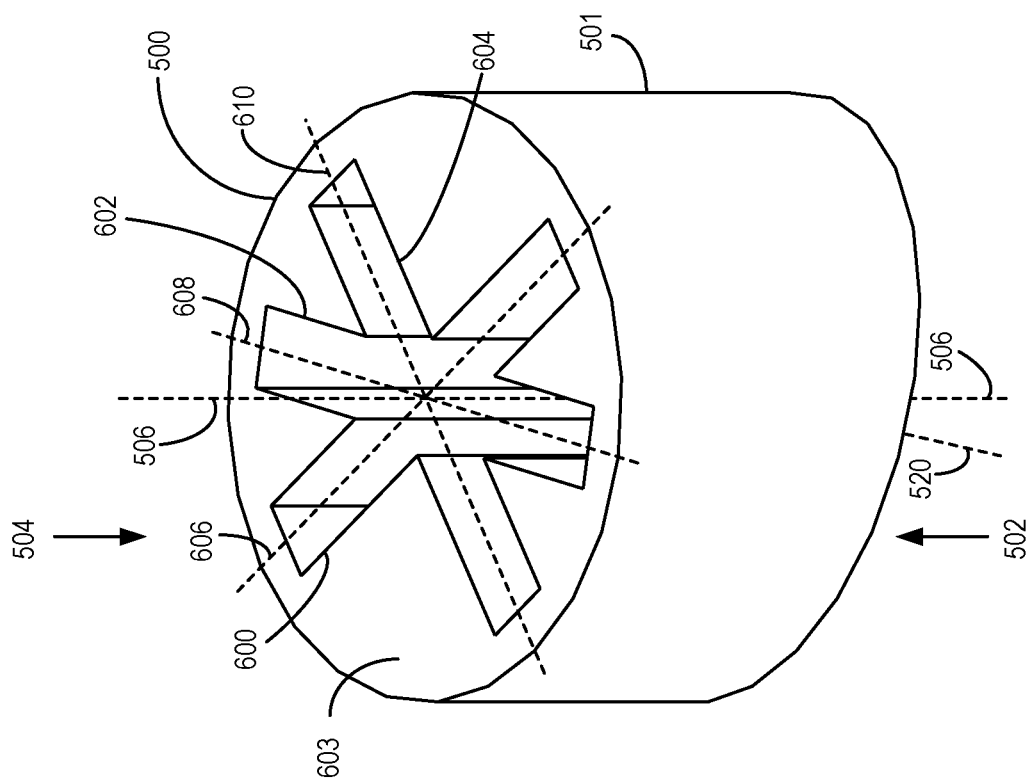
FIG. 6 shows a top perspective view of the ultrasound probe guide of FIG. 5 including a plurality of detents each shaped to receive an ultrasound probe.
Figure 10:
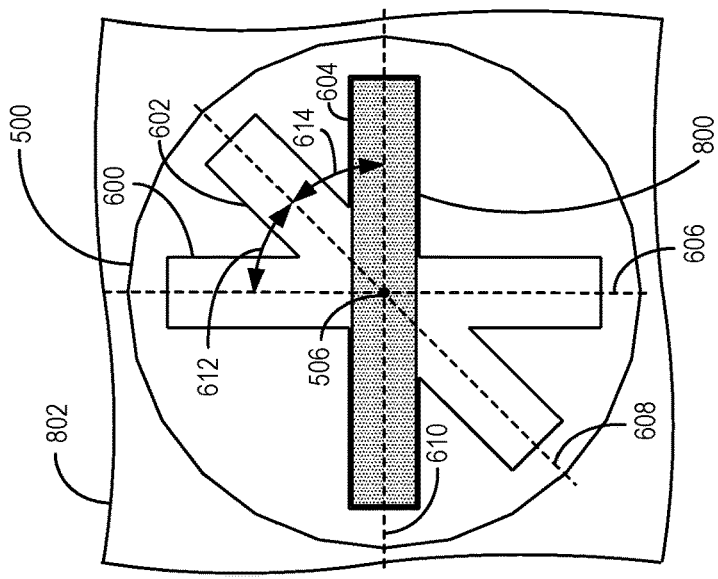
FIG. 10 shows a top view of the ultrasound probe guide of FIGS. 5-9 with the ultrasound probe in a third rotational position.
Figure 9:
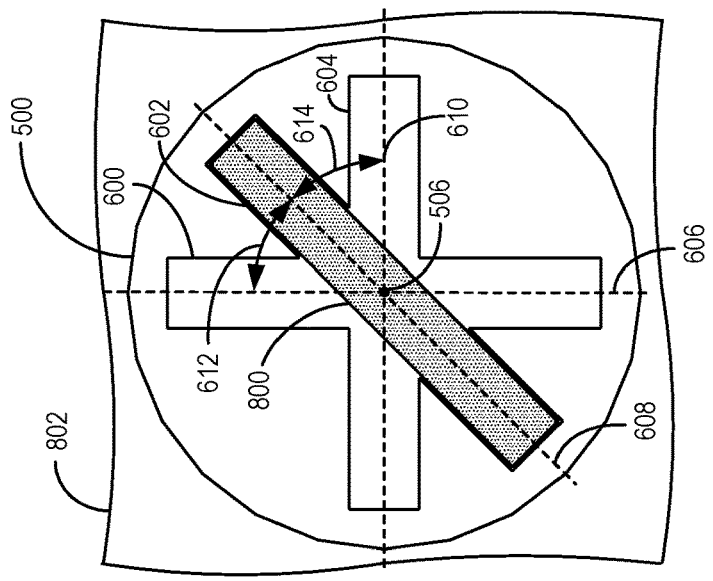
FIG. 9 shows a top view of the ultrasound probe guide of FIGS. 5-8 with the ultrasound probe in a second rotational position.
Figure 8:
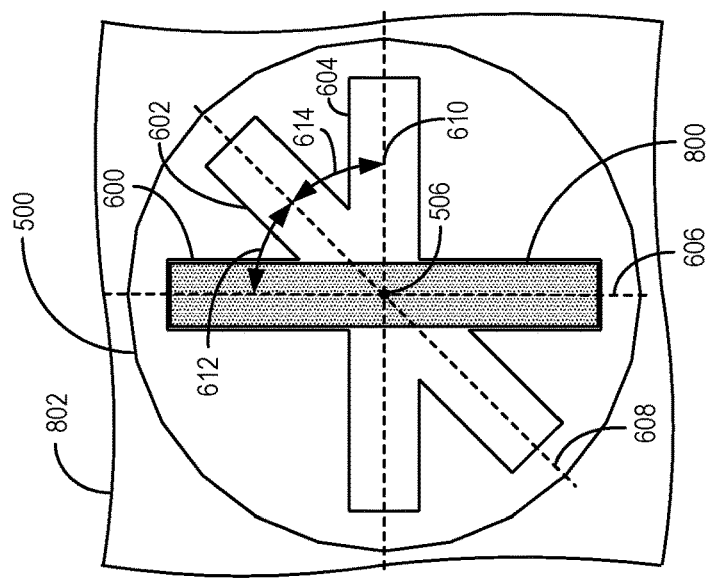
FIG. 8 shows a top view of the ultrasound probe guide of FIGS. 5-7 with an ultrasound probe in a first rotational position.

Referring to FIG. 6, a top perspective view of the ultrasound probe guide 500 of FIG. 5 is shown. The probe guide 500 includes a first detent 600, a second detent 602, and a third detent 604. The first detent 600 extends through the probe guide 500 from the first end 502 to the second end 504. The first detent 600 is arranged along axis 606 extending in a radial direction relative to the central axis 506 and is shaped to receive the ultrasound probe in a first rotational position relative to the probe guide 500 (e.g., as shown by FIG. 8 and described further below). The second detent 602 is arranged along axis 608 extending radially relative to the central axis 506 and is shaped to receive the ultrasound probe in a second rotational position relative to the probe guide 500 (e.g., as shown by FIG. 9 and described further below). The axis 608 is offset from the axis 606 such that the axis 608 is angled relative to the axis 606 around the central axis 506 by angle 612 (shown by FIGS. 8-10). In this configuration, the second detent 602 is angled relative to the first detent 600 around the central axis 506 by the angle 612. In some examples, the angle 612 may be 45 degrees. The third detent 604 is arranged along axis 610 extending radially relative to the central axis 506 and is shaped to receive the ultrasound probe in a third rotational position relative to the probe guide 500 (e.g., as shown by FIG. 10 and described further below). The axis 610 is offset from the axis 608 such that the axis 610 is angled relative to the axis 608 around the central axis 506 by angle 614. In this configuration, the third detent 604 is angled relative to the second detent 602 around the central axis 506 by the angle 614. In some examples, the angle 614 may be 45 degrees.

Referring to FIG. 7, an exploded bottom perspective view of the ultrasound probe guide 500 of FIGS. 5-6 is shown. In the embodiment shown, the probe guide 500 includes a recess 700 formed at the first end 502 and an insert 702 shaped to seat within the recess 700. The insert 702 may be formed from a flexible material as described above (e.g., silicone) and may form the lower end surface 508 of the probe guide 500. During imaging of a subject, ultrasonic pulses generated by the ultrasound probe may be transmitted through the insert 702 at the lower end surface 508 to the subject. However, in other embodiments, the probe guide 500 may not include the insert 702 and the probe guide 500 may maintain the ultrasound probe directly in contact with the imaged subject (e.g., without the insert 702 disposed between the ultrasound probe and the subject).

Referring to FIG. 8, a top view of the ultrasound probe guide 500 of FIGS. 5-7 is shown with an ultrasound probe 800 in a first rotational position. The ultrasound probe described above with reference to FIGS. 5-7 may be the ultrasound probe 800. The ultrasound probe 800 may be similar to, or the same as, the ultrasound probes described above (e.g., ultrasound probe 400 described above with reference to FIG. 4). In the configuration shown by FIG. 8, the ultrasound probe 800 is coupled with the probe guide 500 and is maintained in the first rotational position by the first detent 600 of the probe guide 500. The first detent 600 is engaged by the ultrasound probe 800 such that the ultrasound probe 800 seats within the first detent 600 and is maintained in the first rotational position by interior walls of the first detent 600. A profile of the first detent 600 may be complementary to a profile of the ultrasound probe 800 to reduce a clearance between the first detent 600 and the ultrasound probe 800.

Referring to FIG. 9, a top view of the ultrasound probe guide 500 of FIGS. 5-8 is shown with the ultrasound probe 800 in a second rotational position. The ultrasound probe 800 is shown coupled with the probe guide 500 and is maintained in the second rotational position by the second detent 602. The second detent 602 is engaged by the ultrasound probe 800 such that the ultrasound probe 800 seats within the second detent 602 and is maintained in the second rotational position by the interior walls of the second detent 602. Because the second detent 602 is offset from the first detent 600 by angle 612 around the central axis 506, the second rotational position of the ultrasound probe 800 is offset from the first rotational position by angle 612 (e.g., while the second detent 602 is engaged by the ultrasound probe 800, the ultrasound probe 800 is in the different, second rotational position relative to conditions in which the first detent 600 is engaged by the ultrasound probe 800). A profile of the second detent 602 may be similar to, or the same as, the profile of the first detent 600 (e.g., a rectangular profile shaped to engage with the ultrasound probe 800).

Referring to FIG. 10, a top view of the ultrasound probe guide 500 of FIGS. 5-9 is shown with the ultrasound probe 800 in a third rotational position. The ultrasound probe 800 is shown coupled with the probe guide 500 and is maintained in the third rotational position by the third detent 604. The third detent 604 is engaged by the ultrasound probe 800 such that the ultrasound probe 800 seats within the third detent 604 and is maintained in the third rotational position by the interior walls of the third detent 604. Because the third detent 604 is offset from the second detent 602 by angle 614 around the central axis 506, the third rotational position of the ultrasound probe 800 is offset from the second rotational position by angle 614 (e.g., while the third detent 604 is engaged by the ultrasound probe 800, the ultrasound probe 800 is in the different, third rotational position relative to conditions in which the second detent 602 is engaged by the ultrasound probe 800). A profile of the third detent 604 may be similar to, or the same as, the profile of the first detent 600 and/or the profile of the second detent 602 (e.g., a rectangular profile shaped to engage with the ultrasound probe 800).

In each of FIGS. 8-10, the probe guide 500 is shown in a same position relative to imaged subject 802. The position of the probe guide 500 relative to the subject 802 may be maintained throughout the transition of the ultrasound probe 800 from the first rotational position shown by FIG. 8 to the second rotational position shown by FIG. 9, and from the second rotational position to the third rotational position shown by FIG. 10. Adjusting the ultrasound probe 800 from the first rotational position to the second rotational position may include unseating the ultrasound probe 800 from the first detent 600 (e.g., disengaging the first detent 600 and the ultrasound probe 800), and seating the ultrasound probe 800 within the second detent 602 (e.g., engaging the second detent 602 and the ultrasound probe 800). Adjusting the ultrasound probe 800 from the second rotational position to the third rotational position may include unseating the ultrasound probe 800 from the second detent 602 (e.g., disengaging the second detent 602 and the ultrasound probe 800), and seating the ultrasound probe 800 within the third detent 604 (e.g., engaging the third detent 604 and the ultrasound probe 800). By maintaining the position of the probe guide 500 relative to the subject 802, the controller may determine the position of the ultrasound probe 800 relative to the subject 802 (e.g., similar to the example described above with reference to FIG. 4). As one example, the ultrasound probe 800 may acquire a first image of the subject 802 while the ultrasound probe 800 is engaged with the first detent 600, and the ultrasound probe 800 may acquire a second image of the subject 802 while the ultrasound probe 800 is engaged with the second detent 602.

Because the angle of the second detent 602 relative to the first detent 600 is pre-determined and known by the controller (e.g., angle 612) and because the position of the probe guide 500 is maintained throughout adjustment of the ultrasound probe 800 from the first rotational position (e.g., engagement with the first detent 600) to the second rotational position (e.g., engagement with the second detent 602), the controller may determine that a plane of the first image (e.g., similar to first imaging plane 404 described above with reference to FIG. 4) is angled relative to a plane of the second image (e.g., similar to second imaging plane 406 described above with reference to FIG. 4) by angle 612.

Figure 11:
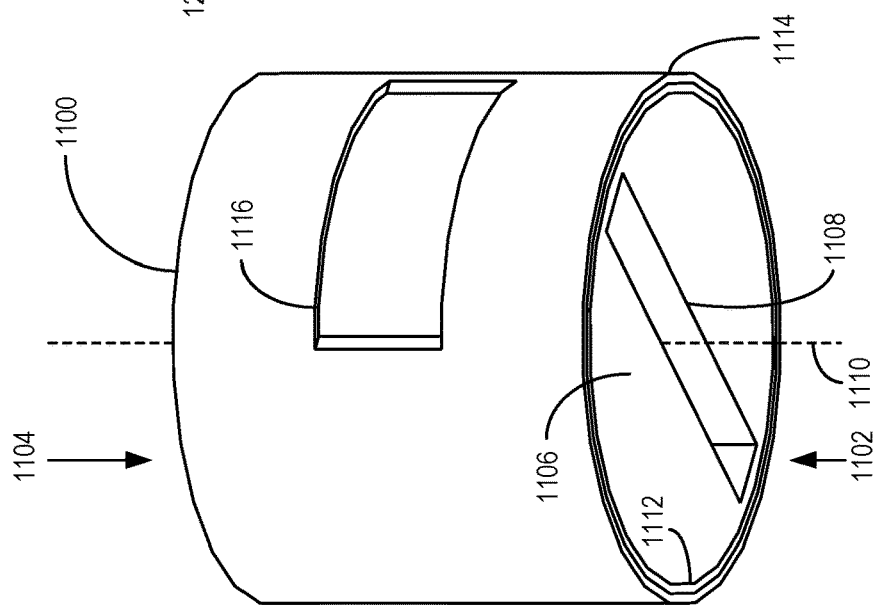
FIG. 11 shows a bottom perspective view of an ultrasound probe guide including rotatable sections according to an embodiment.

Referring to FIG. 11, a bottom perspective view of another ultrasound probe guide 1100 is shown according to an embodiment. The probe guide 1100 may be similar to, or the same as, the probe guide 402 shown by FIG. 4 and described above, the probe guide 302 shown by FIG. 3 and described above, and/or the probe guide 107 shown by FIG. 1 and described above. The probe guide 1100 is configured to receive an ultrasound probe, such as the ultrasound probe 800 shown by FIGS. 8-10 and described above, the ultrasound probe 400 shown by FIG. 4 and described above, the ultrasound probe 300 shown by FIG. 3 and described above, the ultrasound probe 200 shown by FIG. 2 and described above, and/or the ultrasound probe 106 shown by FIG. 1 and described above.

The probe guide 1100 includes a first end 1102 and a second end 1104. During conditions in which the ultrasound probe is coupled with the probe guide 1100, the elements of the ultrasound probe configured to emit pulsed ultrasonic signals (e.g., similar to elements 104 described above with reference to FIG. 1) are arranged closer to the first end 1102 than the second end 1104. In some examples, a portion of the ultrasound probe (e.g., the end portion including the elements configured to emit pulsed ultrasonic signals) may be flush with end surface 1106 or may protrude outward from central detent 1108 at the end surface 1106 at the first end 1102 of the probe guide 1100. The end surface 1106 may be angled relative to an upper end surface 1200 (shown by FIG. 12), similar to the example described above with reference to FIG. 4. While the ultrasound probe is coupled with the probe guide 1100, a central axis of the ultrasound probe may be arranged coaxially with a central axis 1110 of the probe guide 1100.

Figure 13:
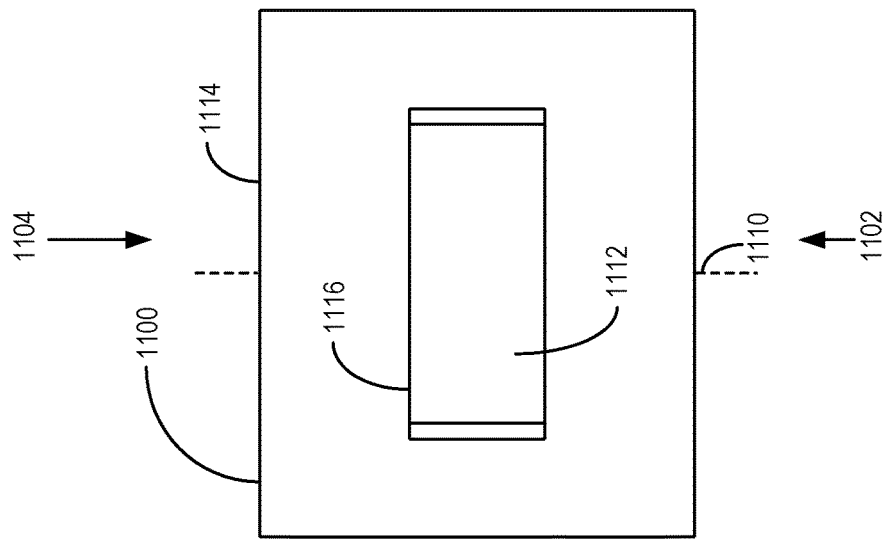
FIG. 13 shows a side view of the ultrasound probe guide of FIGS. 11-12.

The probe guide 1100 includes an inner section 1112 and an outer section 1114, where the inner section 1112 and the outer section 1114 rotatably couple with each other. The inner section 1112 and outer section 1114 may be referred to herein together as a body of the probe guide 1100. The inner section 1112 is coupled with the outer section 1114 such that the inner section 1112 may rotate relative to the outer section 1114, as described below. The outer section 1114 may include a side opening 1116 through which an operator of the ultrasound imaging system including the probe guide 1100 may rotate the inner section 1112 relative to the outer section 1114, in some embodiments. In particular, the inner section 1112 may be visible through the outer section 1114, as shown by FIG. 13. In some embodiments, the inner section 1112 and/or outer section 1114 may include a wheel or other device configured to rotate the inner section 1112 relative to the outer section 1114 during conditions in which the wheel is rotated by the operator. In other embodiments and as described below, the probe guide 1100 may include a motor configured to rotate the inner section 1112 relative to the outer section 1114. It should be appreciated that although rotation of the inner section 1112 relative to the outer section 1114 is described herein, in some embodiments the outer section 1114 may rotate relative to the inner section 1112.

Figure 12:
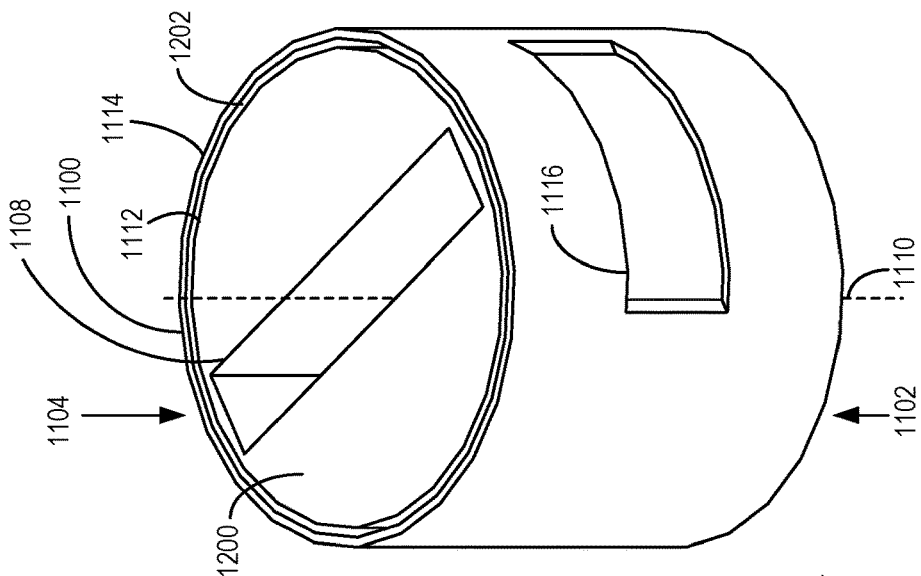
FIG. 12 shows a top perspective view of the ultrasound probe guide of FIG. 11.

Referring to FIG. 12, a top perspective view of the ultrasound probe guide 1100 of FIG. 11 is shown. A clearance 1202 is shown between the inner section 1112 and the outer section 1114. The clearance 1202 may increase an ease of rotation of the inner section 1112 relative to the outer section 1114.

Figure 14:
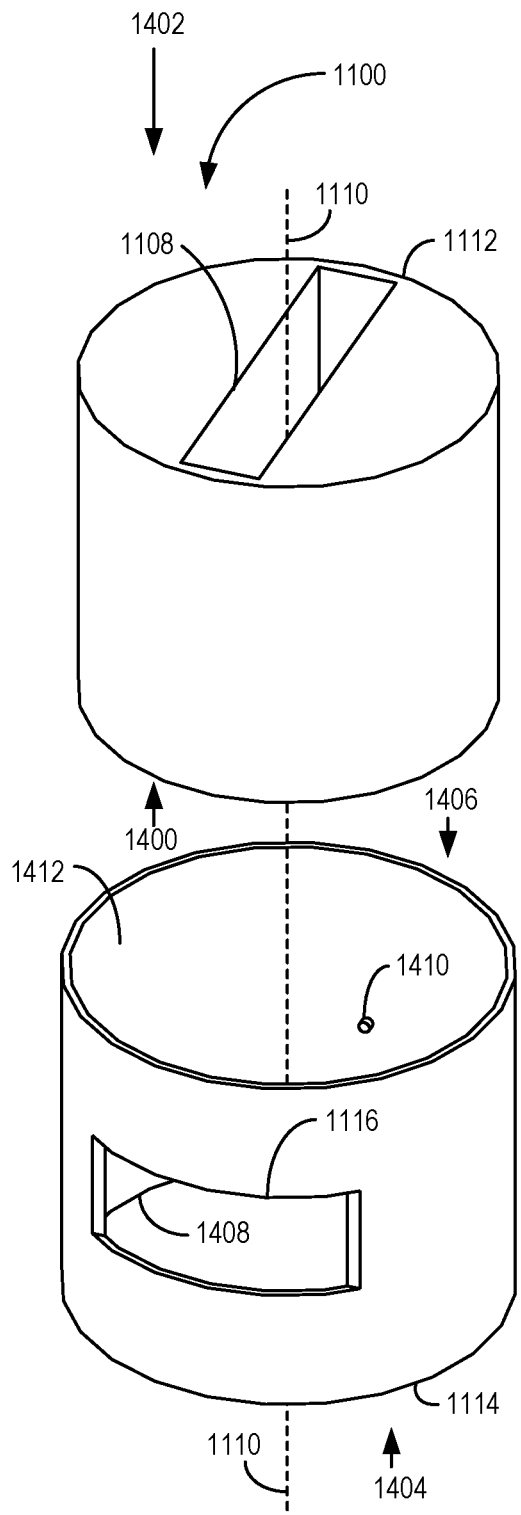
FIG. 14 shows an exploded top perspective view of the ultrasound probe guide of FIGS. 11-13.

Referring to FIG. 14, an exploded top perspective view of the ultrasound probe guide 1100 of FIGS. 11-13 is shown. FIG. 14 shows the inner section 1112 and the outer section 1114 decoupled from each other. The inner section 1112 includes a first end 1400 and a second end 1402, and the outer section 1114 includes a first end 1404 and a second end 1406. During conditions in which the inner section 1112 and the outer section 1114 are coupled to each other, the first end 1400 of the inner section 1112 is arranged at the first end 1404 of the outer section 1114, and the second end 1402 of the inner section 1112 is arranged at the second end 1406 of the outer section 1114. The first end 1400 of the inner section 1112 including end surface 1106 may be encircled by a lower opening 1408 at the first end 1404 of the outer section 1114.

As shown by FIG. 14, the outer section 1114 includes a protrusion 1410 arranged at an inner surface 1412 of the outer section 1114. The protrusion 1410 is shaped to engage with detents of the inner section 1112, as described below.

Figure 15:
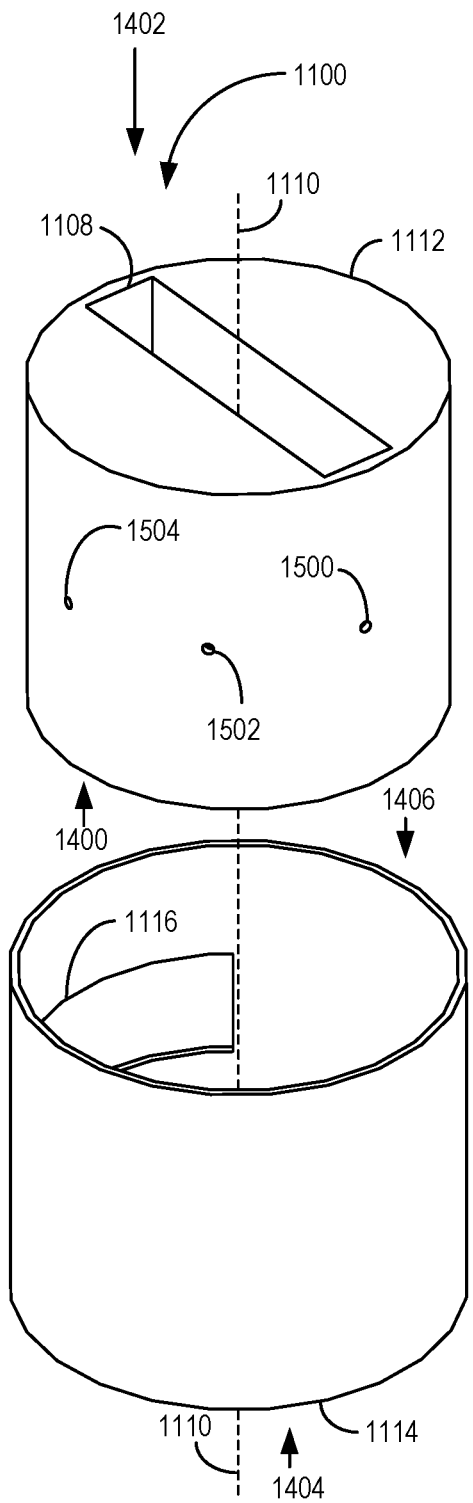
FIG. 15 shows an exploded bottom perspective view of the ultrasound probe guide of FIGS. 11-14.

Referring to FIG. 15, an exploded bottom perspective view of the ultrasound probe guide 1100 of FIGS. 11-14 is shown. The inner section 1112 is shown including a first detent 1500, a second detent 1502, and a third detent 1504. During conditions in which the inner section 1112 and the outer section 1114 are coupled together, the protrusion 1410 of the outer section 1114 (shown by FIG. 14) may engage with any of the first detent 1500, the second detent 1502, or the third detent 1504 in order to maintain a rotational position of the inner section 1112 relative to the outer section 1114, as described below. In particular, the protrusion 1410 may seat within any of the first detent 1500, the second detent 1502, or the third detent 1504 in order to maintain the inner section 1112 in a first rotational position, a second rotational position, or a third rotational position, respectively, relative to the outer section 1114, as described below.

Figure 16:
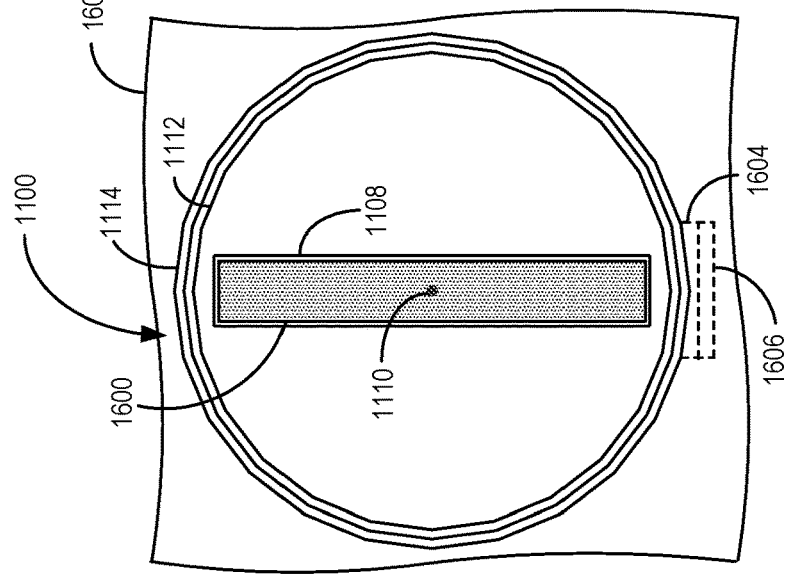
FIG. 16 shows a top view of the ultrasound probe guide of FIGS. 11-15 with an ultrasound probe in a first rotational position.

Referring to FIG. 16, a top view of the ultrasound probe guide 1100 of FIGS. 11-15 is shown with an ultrasound probe 1600 in a first rotational position. In the configuration shown by FIG. 16, the first detent 1500 (shown by FIG. 15) is engaged with the protrusion 1410 (shown by FIG. 14) such that the inner section 1112 is maintained in the first rotational position relative to the outer section 1114. Because the ultrasound probe 1600 seats within the central detent 1108 and the orientation of the ultrasound probe 1600 relative to the inner section 1112 is maintained by the central detent 1108, the rotational position of the ultrasound probe 1600 corresponds to the rotational position of the inner section 1112 relative to the outer section 1114. In particular, the ultrasound probe 1600 does not rotate within the central detent 1108, but the ultrasound probe 1600 and inner section 1112 may rotate together as a single unit relative to the outer section 1114. During imaging of a subject 1602, the position of the probe guide 1100 may be maintained relative to the subject 1602 (e.g., the probe guide 1100 may be maintained in a same translational position relative to the subject 1602) and position of the ultrasound probe 1600 may be adjusted relative to the subject 1602 via engagement of different the detents of the probe guide 1100.

Figure 17:
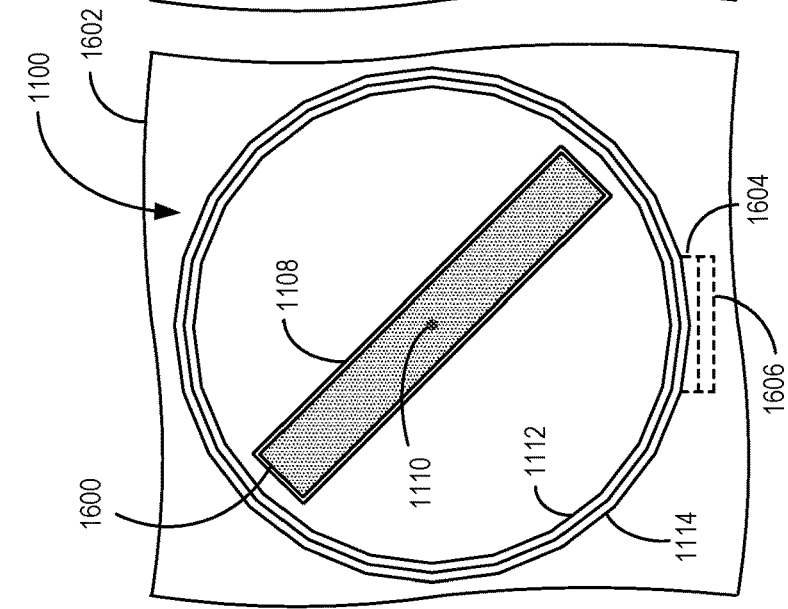
FIG. 17 shows a top view of the ultrasound probe guide of FIGS. 11-16 with an ultrasound probe in a second rotational position.

For example, as shown by FIG. 17, the ultrasound probe 1600 is shown coupled with the probe guide 1100 and in a second rotational position. In the configuration shown by FIG. 17, the second detent 1502 (shown by FIG. 15) is engaged with the protrusion 1410 (shown by FIG. 14), and the first detent 1500 and third detent 1504 are not engaged with the protrusion 1410. As one example, the inner section 1112 and ultrasound probe 1600 may be rotated together as a single unit relative to the outer section 1114 from the first rotational position shown by FIG. 16 to the second rotational position shown by FIG. 17. Rotating the inner section 1112 and the ultrasound probe 1600 from the first rotational position to the second rotational position includes disengaging the first detent 1500 from the protrusion 1410 and engaging the second detent 1502 with the protrusion 1410. The second detent 1502 locks the position of the inner section 1112 and the ultrasound probe 1600 and maintains the inner section 1112 and the ultrasound probe 1600 in the second rotational position. The inner section 1112 and ultrasound probe 1600 may be rotated together without rotation of the outer section 1114 such that the position of the outer section 1114 is maintained relative to the subject 1602.

Figure 18:
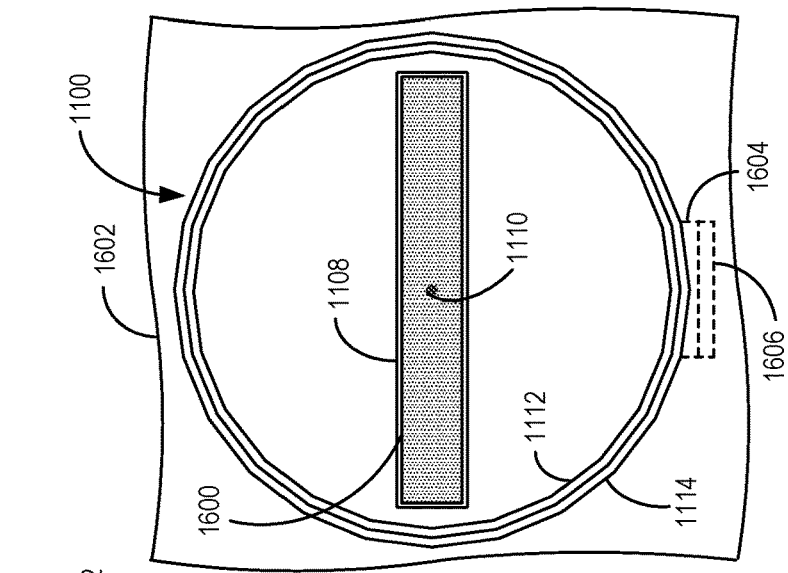
FIG. 18 shows a top view of the ultrasound probe guide of FIGS. 11-17 with an ultrasound probe in a third rotational position.

The inner section 1112 and ultrasound probe 1600 may further be rotated together from the second rotational position shown by FIG. 17 to the third rotational position shown by FIG. 18. In the configuration shown by FIG. 18, the protrusion 1410 (shown by FIG. 14) is engaged with the third detent 1504 (shown by FIG. 15), and the rotational position of the inner section 1112 and the ultrasound probe 1600 is maintained by the third detent 1504. The third rotational position may be offset around the central axis 1110 of the probe guide 1100 from the second rotational position by a first amount of angle (e.g., 45 degrees, similar to the example described above with reference to FIGS. 8-10), and the second rotational position may be offset around the central axis 1110 of the probe guide 1100 from the first rotational position by a second amount of angle (e.g., 45 degrees). During a scan of the subject 802, a first image of the subject 802 may be acquired with the ultrasound probe 1600 and inner section 1112 in the first rotational position shown by FIG. 16, a second image of the subject 802 may be acquired with the ultrasound probe 1600 and inner section 1112 in the second rotational position shown by FIG. 17, and a third image of the subject may be acquired with the ultrasound probe 1600 and inner section 1112 in the third rotational position shown by FIG. 18. The controller may determine (e.g., calculate) a volume flow rate of blood through a vessel at the imaged location of the subject 1602 based on the first image, the second image, and the third image, as described above (e.g., similar to the example described above with reference to FIG. 4).

In some embodiments, the probe guide 1100 may include a motor 1604 configured to adjust the rotational position of the inner section 1112 relative to the outer section 1114. The motor 1604 may be controlled by the operator of the ultrasound imaging system including the probe guide 1100 via a motor interface 1606, in some embodiments. The motor interface 1606 may be arranged at an exterior of the outer section 1114 in some examples. In other examples the motor interface 1606 may be integrated with a user interface of the ultrasound imaging system (e.g., input device 115 shown by FIG. 1 and described above). As yet other example, the motor 1604 may be controlled via a graphical user interface of the ultrasound imaging system and may communicate electronically with the controller of the ultrasound imaging system (e.g., controller 114 shown by FIG. 1 and described above) via a wired connection (e.g., a cable joining the probe guide 1100 electronically to the controller)

and/or a wireless connection (e.g., a Wi-Fi connection between the probe guide 1100 and the controller).

The motor 1604 may control the rotational position of the inner section 1112 during conditions in which the ultrasound probe 1600 is coupled with the probe guide 1100 (e.g., seated within the central detent 1108). In some embodiments, the motor 1604 may automatically rotate the inner section 1112 while the ultrasound probe 1600 is coupled to the central detent 1108 according to an imaging routine of the ultrasound imaging system.

In an example operation of the ultrasound imaging system including the probe guide 1100 with motor 1604, the operator of the ultrasound imaging system may position the probe guide 1100 at the desired location of the subject to be imaged (e.g., at a vessel of the subject, such as the vessel 408 shown by FIG. 4 and described above) and may seat the ultrasound probe 1600 within the central detent 1108. The operator may initiate the imaging routine of the ultrasound imaging system (e.g., the operator may input a command to the user interface of the ultrasound imaging system to initiate imaging of the subject via the ultrasound probe 1600 and probe guide 1100).

During the imaging routine, the control may first acquire a first image of an anatomy of the subject (e.g., a vessel, similar to the vessel 408 described above with reference to FIG. 4) while the ultrasound probe 1600 is in the first rotational position shown by FIG. 16. The controller may then command the motor 1604 electronically to rotate the inner section 1112 of the probe guide 1100 from the first rotational position to the second rotational position shown by FIG. 17, where adjustment of the inner section 1112 from the first rotational position to the second rotational position includes disengaging the first detent 1500 of the probe guide 1100 (e.g., unseating the protrusion 1410 from the first detent 1500) and engaging the second detent 1502 of the probe guide 1100 (e.g., seating the protrusion 1410 against the second detent 1502). Because the ultrasound probe 1600 is seated within the central detent 1108 of the inner section 1112, as the inner section 1112 is rotated from the first rotational position to the second rotational position by the motor 1604, the ultrasound probe 1600 is similarly rotated from the first rotational position to the second rotational position. A second image of the anatomy of the subject may then be acquired via the ultrasound probe 1600 while the ultrasound probe 1600 is maintained in the second rotational position by the probe guide 1100. The controller may then command the motor 1604 electronically to rotate the inner section 1112 of the probe guide 1100 from the second rotational position to the third rotational position shown by FIG. 18, where adjustment of the inner section 1112 from the second rotational position to the third rotational position includes disengaging the second detent 1502 of the probe guide 1100 (e.g., unseating the protrusion 1410 from the second detent 1502) and engaging the third detent 1504 of the probe guide 1100 (e.g., seating the protrusion 1410 against the third detent 1504). A third image of the anatomy of the subject may then be acquired via the ultrasound probe 1600 while the ultrasound probe 1600 is maintained in the third rotational position by the probe guide 1100. The controller may then determine (e.g., calculate) the volume flow rate through the anatomy of the subject according to the methods described herein (e.g., similar to the calculation described above with reference to FIG. 4).

Figure 19:
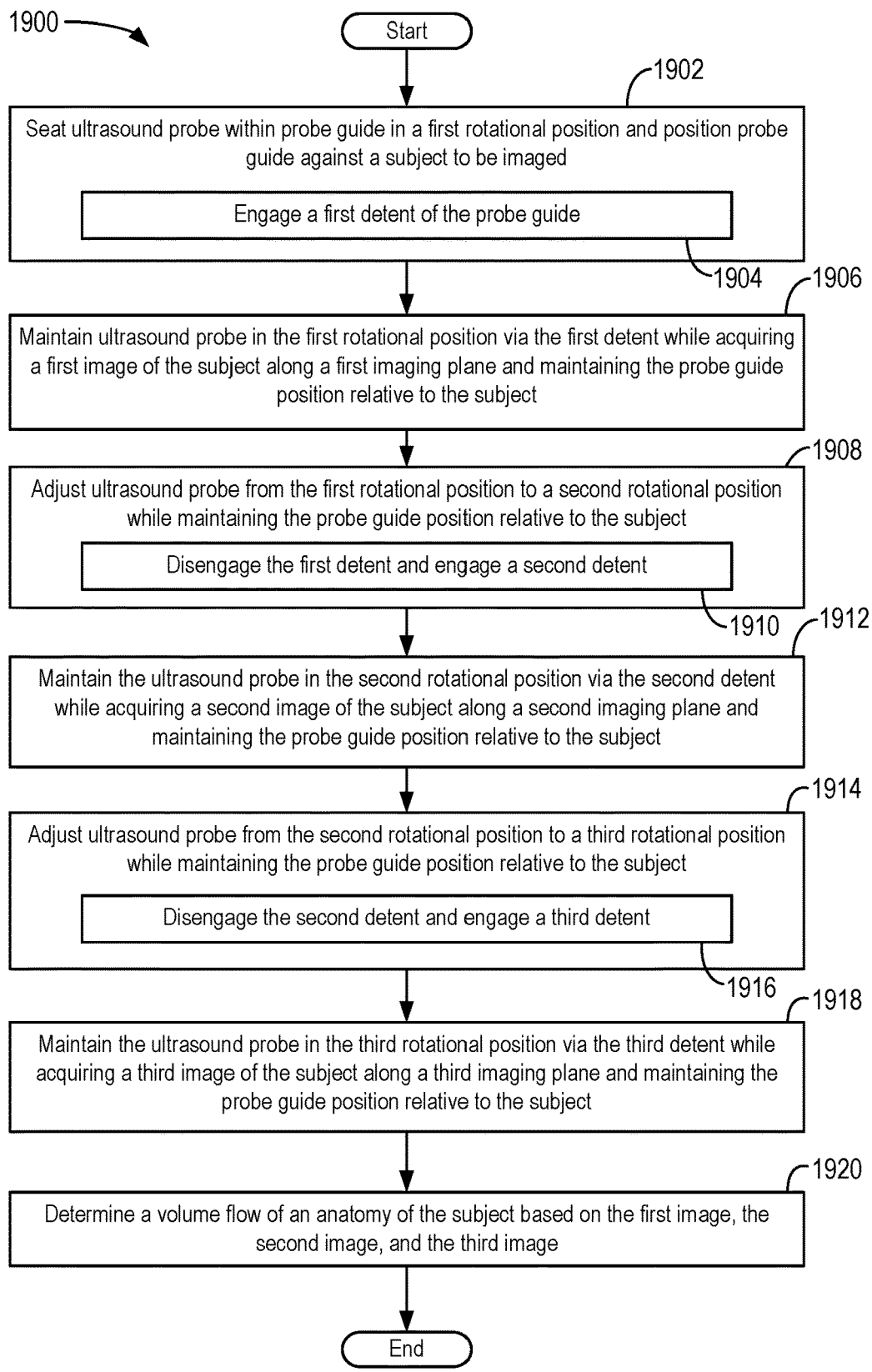
FIG. 19 shows a flowchart illustrating a method for imaging a subject via an ultrasound probe and ultrasound probe guide according to an embodiment.

FIG. 19 shows a flowchart illustrating a method 1900 for imaging a subject via an ultrasound imaging system including an ultrasound probe and an ultrasound probe guide. The ultrasound imaging system, ultrasound probe, and ultrasound probe guide may be similar to, or the same as, the ultrasound imaging system 100, ultrasound probe 106, and ultrasound probe guide 107, respectively, described above with reference to FIG. 1. In some embodiments, the ultrasound probe and ultrasound probe guide may be similar to, or the same as, the ultrasound probe 400 and ultrasound probe guide 402, respectively, described above with reference to FIG. 4. In some embodiments, the ultrasound probe and ultrasound probe guide may be similar to, or the same as, the ultrasound probe 800 and ultrasound probe guide 500, respectively, described above with reference to FIGS. 8-10. In some embodiments, the ultrasound probe and ultrasound probe guide may be similar to, or the same as, the ultrasound probe 1600 and ultrasound probe guide 1100, respectively, described above with reference to FIGS. 16-18.

Instructions for carrying out method 1900 and the rest of the methods included herein may be executed by a controller based on instructions stored on a memory of the controller and in conjunction with signals received from sensors of the ultrasound imaging system, such as the sensors described above with reference to FIG. 1. The controller may employ actuators of the ultrasound imaging system to adjust system operation, according to the methods described below. As one example, the controller may adjust operation of the probe guide by controlling a motor of the probe guide (e.g., similar to, or the same as, the motor 1604 shown by FIGS. 16-18 and described above) based on instructions stored on a memory of the controller and/or signals received by the controller from the probe guide. For example, adjusting a rotational position of an inner section of the probe guide (e.g., similar to the inner section 1112 described above with reference to FIGS. 11-18) may include adjusting an energization of the motor to rotate the inner section.

The method 1900 at 1902 includes seating the ultrasound probe within the probe guide in a first rotational position and positioning the probe guide against a subject to be imaged. The probe guide may include a first end and an opposing second end, where elements of the ultrasound probe configured to emit ultrasonic pulses are arranged at the first end during conditions in which the ultrasound probe is seated within the probe guide. Seating the ultrasound probe within the probe guide may include inserting the ultrasound probe through the second end of the probe guide and in alignment with a central axis of the probe guide.

Seating the ultrasound probe within the probe guide in the first rotational position and positioning the probe guide against the subject to be imaged at 1902 includes, at 1904, engaging a first detent of the probe guide. Engaging the first detent may include positioning the ultrasound probe within the first detent and seating the ultrasound probe against interior surfaces of the first detent to maintain the rotational position of the ultrasound probe relative to the probe guide, similar to the example described above with reference to FIG. 8. In other embodiments, engaging the first detent may include seating a protrusion of the probe guide within the first detent to maintain the rotational position of the ultrasound probe relative to the probe guide, similar to the example described above with reference to FIG. 16.

The method continues from 1902 and 1904 to 1906 where the method includes maintaining the ultrasound probe in the first rotational position via the first detent while acquiring a first image of the subject along a first imaging plane and maintaining the probe guide position relative to the subject. The first imaging plane may be similar to, or the same as, the first imaging plane 404 described above with reference to FIG. 4. Maintaining the probe guide position relative to the subject includes not adjusting the translational position of the probe guide relative to the subject (e.g., maintaining the probe guide at the desired anatomy of the subject to be imaged).

The method continues from 1906 to 1908 where the method includes adjusting the ultrasound probe from the first rotational position to a second rotational position while maintaining the probe guide position relative to the subject. Adjusting the ultrasound probe from the first rotational position to the second rotational position may include rotating the ultrasound probe along the central axis of the probe guide.

Adjusting the ultrasound probe from the first rotational position to the second rotational position while maintaining the probe guide position relative to the subject at 1908 includes, at 1910, disengaging the first detent and engaging a second detent. In some examples, disengaging the first detent may include unseating the ultrasound probe from the first detent. In other examples, disengaging the first detent may include unseating the protrusion of the probe guide from the first detent. Engaging the second detent may include seating the ultrasound probe against the second detent, in some examples. In other examples, engaging the second detent may include seating the protrusion of the probe guide within the second detent (e.g., by rotating the inner section of the probe guide relative to the outer section).

The method continues from 1908 and 1910 to 1912 where the method includes maintaining the ultrasound probe in the second rotational position via the second detent while acquiring a second image of the subject along a second imaging plane and maintaining the probe guide position relative to the subject. The second imaging plane may be similar to, or the same as, the second imaging plane 406 described above with reference to FIG. 4. Maintaining the probe guide position relative to the subject includes not adjusting the translational position of the probe guide relative to the subject (e.g., maintaining the probe guide at the desired anatomy of the subject to be imaged).

The method continues from 1912 to 1914 where the method includes adjusting the ultrasound probe from the second rotational position to a third rotational position while maintaining the probe guide position relative to the subject. Adjusting the ultrasound probe from the first rotational position to the second rotational position may include rotating the ultrasound probe along the central axis of the probe guide.

Adjusting the ultrasound probe from the second rotational position to the third rotational position while maintaining the probe guide position relative to the subject at 1914 includes, at 1916, disengaging the second detent and engaging a third detent. In some examples, disengaging the second detent may include unseating the ultrasound probe from the second detent. In other examples, disengaging the second detent may include unseating the protrusion of the probe guide from the second detent. Engaging the third detent may include seating the ultrasound probe against the third detent, in some examples. In other examples, engaging the third detent may include seating the protrusion of the probe guide within the third detent (e.g., by rotating the inner section of the probe guide relative to the outer section)

The method continues from 1914 and 1916 to 1918 where the method includes maintaining the ultrasound probe in the third rotational position via the third detent while acquiring a third image of the subject along a third imaging plane and maintaining the probe guide position relative to the subject. The third imaging plane may be similar to, or the same as, the third imaging plane 407 described above with reference to FIG. 4. Maintaining the probe guide position relative to the subject includes not adjusting the translational position of the probe guide relative to the subject (e.g., maintaining the probe guide at the desired anatomy of the subject to be imaged).

The method continues from 1918 to 1920 where the method includes determining a volume flow of an anatomy of the subject based on the first image, the second image, and the third image. In some examples, the controller may determine the volume flow of the anatomy (e.g., volume flow rate) according to functions stored in the memory of the controller (e.g., similar to the examples described above with reference to FIG. 4). The determination (e.g., calculation) of the volume flow rate may be based at least in part on the angles between the three imaging planes, where the angles may be pre-determined by the configuration of the probe guide and known to the controller. For example, the first imaging plane may be orthogonal to the third imaging plane, and the second imaging plane may be oblique to each of the first imaging plane and the third imaging plane. Similarly, the first rotational position may be orthogonal to the third rotational position, and the second rotational position may be oblique relative to the first rotational position and the third rotational position (e.g., the second rotational position may be offset from the first rotational position by 45 degrees around the central axis of the probe guide, and the third rotational position may be offset from the first rotational position by 90 degrees around the central axis of the probe guide and offset from the second rotational position by 45 degrees around the central axis of the probe guide).

Figure 20:
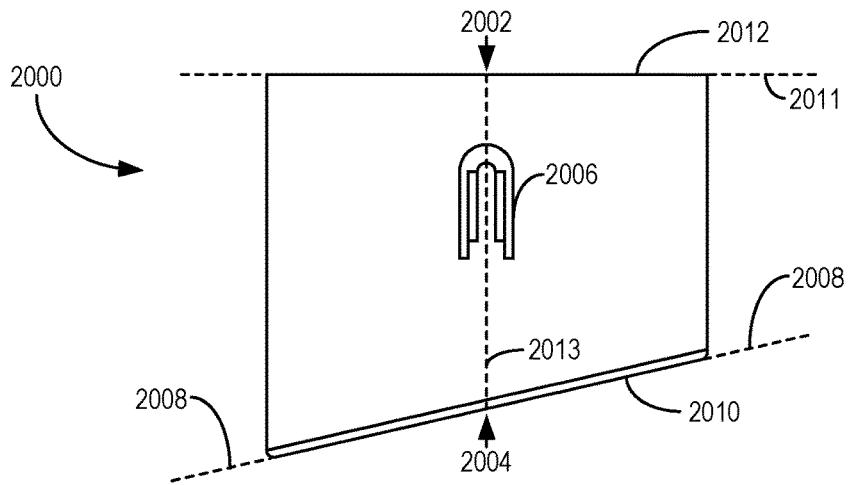
FIG. 20 shows a side view of an outer section of an ultrasound probe guide including an angled lower end, according to an embodiment.

Referring to FIG. 20, a side view of an outer section 2000 of an ultrasound probe guide is shown. The outer section 2000 may be configured to couple with an inner section and may be rotatable relative to the inner section, similar to the example described above with reference to FIGS. 11-18. The outer section 2000 includes an upper end surface 2012 arranged at a first end 2002 and a lower end surface 2010 arranged at a second end 2004 along a central axis 2013 of the outer section 2000, where the first end 2002 and second end 2004 are opposite to each other. The lower end surface 2010 is angled relative to the upper end surface 2012. For example, axis 2008 is shown arranged parallel with the lower end surface 2010 and axis 2011 is shown arranged parallel with the upper end surface 2012, and the axis 2008 is angled relative to the axis 2011. The angle between axis 2008 and axis 2011 may be between 10-15 degrees, in some examples. A plurality of clips formed by the outer section 2000 may maintain the outer section 2000 in engagement with the inner section during conditions in which the inner section and the outer section 2000 are coupled together. In the example shown, the outer section 2000 forms a first clip 2006, a second clip 2007 (shown by FIG. 21), a third clip 2009 (shown by FIG. 21), and a fourth clip 2200 (shown by FIG. 22). However, in other examples, the outer section 2000 may include a different number and/or relative arrangement of clips.

Figure 21:
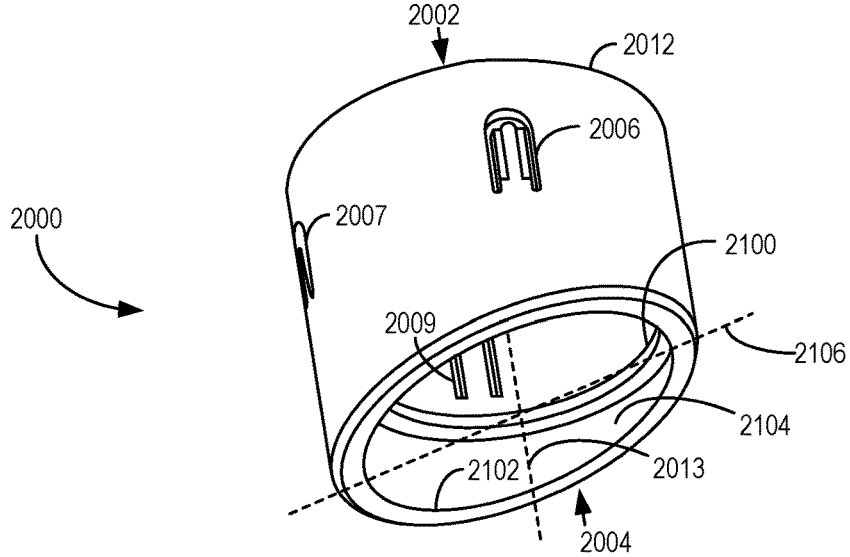
FIG. 21 shows a perspective view of the ultrasound probe guide of FIG. 20.

Referring to FIG. 21, a perspective view of the outer section 2000 is shown. The outer section 2000 includes a first rim 2102 and a second rim 2100 formed within an interior of the outer section 2000. The first rim 2102 is an annular edge arranged at the second end 2004 of the outer section 2000. The first rim 2102 extends toward the central axis 2013 from an interior surface 2104 of the outer section 2000. The second rim 2100 is offset from the first rim 2102 in the direction of the central axis 2013 (e.g., away from the second end 2004 and in the direction toward the first end 2002). A flexible insert may seat within the outer section 2000 and be maintained in position by the first rim 2102 and second rim 2100, as described below.

Figure 22:
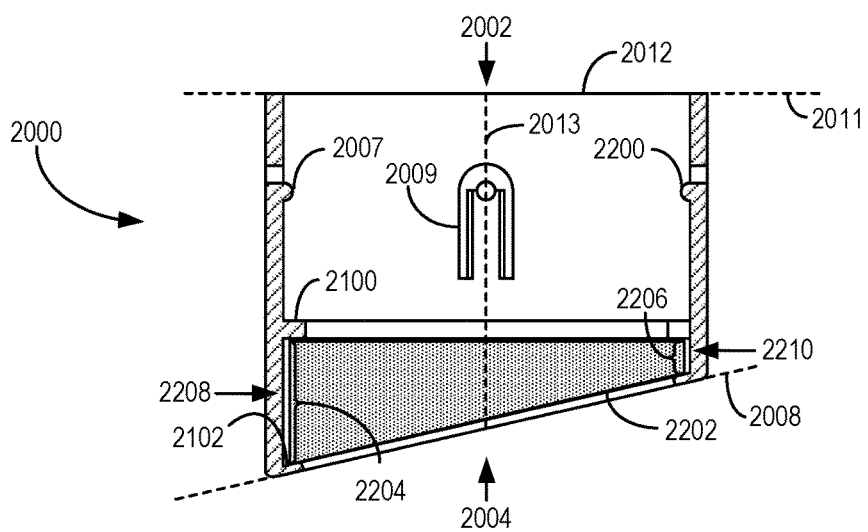
FIG. 22 shows a cross-sectional view of the ultrasound probe guide of FIGS. 20-21 with a flexible insert seated within the outer section at the angled lower end.

Referring to FIG. 22, a cross-sectional view of the outer section 2000 is shown. The view of FIG. 22 may be taken along an axis radial to the central axis 2013 of the outer section 2000, such as the axis 2106 shown by FIG. 21. In the view shown by FIG. 22, a flexible insert 2202 is seated within the outer section 2000 between the first rim 2102 and the second rim 2100. The flexible insert 2202 may be formed from a flexible material (e.g., silicone), similar to the examples described above. A first side 2208 of the flexible insert 2202 may have a first width 2204 and an opposing, second side 2210 of the flexible insert 2202 may have a second width 2206, where the second width 2206 is smaller than the first width 2204. The first width 2204 and the second width 2206 are each in a same direction parallel with the central axis 2013. The flexible insert 2202 may transmit ultrasonic pulses generated by elements of an ultrasound probe coupled with the probe guide to the imaged subject, where the probe guide includes the outer section 2000.

In this way, by controlling the rotational position of the ultrasound probe via the probe guide as described above, a consistency of imaging and/or an imaging quality may be increased. As one example, because the fixed rotational positions provided by the probe guide may be known to the controller, the controller may determine the rotational position of the ultrasound probe during acquisition of each image without additional position sensors and/or without a position sensing system. As a result, a cost of the ultrasound imaging system may be reduced. As another example, because the probe guide maintains the rotational position of the ultrasound probe during acquisition of images by the ultrasound probe, a likelihood of image degradation due to undesired movement of the ultrasound probe may be reduced and imaging quality may be increased.

The technical effect of the probe guide is to maintain the rotational position of the ultrasound probe relative to the imaged subject and to provide a plurality of pre-determined fixed rotational positions for the ultrasound probe.

FIGS. 2-18 and 20-22 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Note that the example routines included herein can be used with various ultrasound imaging system configurations. The methods and routines disclosed herein may be stored as executable instructions in non-transitory memory and may be carried out by the control system including the controller in combination with the various sensors, actuators, and other hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations, and/or functions may be repeatedly performed depending on the particular strategy being used. Further, the described actions, operations, and/or functions may graphically represent code to be programmed into non-transitory memory of the computer readable storage medium in the control system, where the described actions are carried out by executing the instructions in a system including the various hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to other types of ultrasound probes. Moreover, unless explicitly stated to the contrary, the terms "first," "second," "third," and the like are not intended to denote any order, position, quantity, or importance, but rather are used merely as labels to distinguish one element from another. The subject matter of the present disclosure includes all novel and non-obvious combinations and sub-combinations of the various systems and configurations, and other features, functions, and/or properties disclosed herein.

As used herein, the term "approximately" is construed to mean plus or minus five percent of the range unless otherwise specified.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A probe guide, comprising:
a body shaped to seat an ultrasound probe, and including
a first detent shaped to maintain the ultrasound probe in a first rotational position along an axis of the body and a second detent shaped to maintain the ultrasound probe in a second rotational position along the axis of the body, wherein the first detent and the second detent intersect with one another and extend from an upper end surface of the body to an insert of the body, and wherein the body is in a same position relative to an imaged subject throughout a transition of the ultrasound probe directly within the body from the first rotational position to other rotational positions including the second rotational position.

2. The probe guide of claim 1, further comprising a third detent offset from each of the first detent and the second detent and shaped to maintain the ultrasound probe in a third rotational position along the axis of the body, wherein there are no intervening components between the body and the ultrasound probe.

3. The probe guide of claim 2, wherein the first detent, the second detent and the third detent each intersect with one another.

4. The probe guide of claim 3, wherein the insert is flexible and seated within a recess of the body.

5. The probe guide of claim 1, wherein the body includes an inner section and an outer section rotatably coupled with each other, with the inner section including the first detent and the second detent and the outer section including a protrusion shaped to engage with the first detent and the second detent.

6. The probe guide of claim 5, wherein, while engaged with the first detent, the protrusion is disengaged from the second detent.

7. The probe guide of claim 5, further comprising a motor configured to rotate the inner section relative to the outer section or vice versa without decoupling the ultrasound probe from the body.

8. The probe guide of claim 5, further comprising a side opening formed in the outer section, with the side opening extending to a clearance between the inner section and the outer section.

9. A method, comprising:
adjusting an ultrasound probe to a plurality of fixed rotational positions defined by a plurality of detents of a probe guide in which the ultrasound probe is seated via a side opening in the probe guide, the plurality of detents intersecting with one another and extending from an upper end surface of the probe guide to an insert of the probe guide, wherein the ultrasound probe is rotated directly within the probe guide;
acquiring a plurality of images of a subject via the ultrasound probe, the plurality of images comprising a respective image for each rotational position of the plurality of fixed rotational positions; and
throughout an entire duration of the adjusting of the ultrasound probe to the plurality of fixed rotational positions, maintaining a position of the probe guide relative to the subject.

10. The method of claim 9, wherein a first end of the probe guide is angled relative to a second end of the probe guide.

11. The method of claim 9, further comprising determining a volume flow rate of an anatomy of the subject based on the plurality of images.

12. The method of claim 9, wherein adjusting the ultrasound probe to the plurality of fixed rotational positions defined by the probe guide includes:
adjusting the ultrasound probe to a first rotational position by engaging a first detent of the plurality of detents of the probe guide;
adjusting the ultrasound probe to a second rotational position offset from the first rotational position around an axis of the probe guide by engaging a second detent of the plurality of detents of the probe guide; and
adjusting the ultrasound probe to a third rotational position offset from each of the first rotational position and the second rotational position around the axis of the probe guide by engaging a third detent of the plurality of detents of the probe guide, wherein a central axis of the ultrasound probe is maintained coaxial with a central axis of the probe guide throughout adjusting the ultrasound probe to first, second, and third rotational positions.

13. The method of claim 12, wherein engaging the first detent includes seating the ultrasound probe against the first detent, and engaging the second detent includes seating the ultrasound probe against the second detent, and wherein the ultrasound probe is in face-sharing contact with the probe guide when seated against the first detent or the second detent.

14. The method of claim 12, wherein engaging the first detent includes seating a protrusion of the probe guide against the first detent, and engaging the second detent includes seating the protrusion against the second detent.

15. A system, comprising:
an ultrasound probe; and
a probe guide shaped to directly seat the ultrasound probe and maintain a rotational position of the ultrasound probe in any of a plurality of fixed rotational positions along an axis of the probe guide, the plurality of fixed rotational positions defined by a plurality of detents of the probe guide, wherein the plurality of detents intersect with one another and extend only within a 90 degree range from an upper end surface of the probe guide to an insert of the probe guide, and wherein the ultrasound probe is rotated within the probe guide to seat against any of the plurality of detents.

16. The system of claim 15, wherein the plurality of detents includes a first detent defining a first rotational position of the plurality of fixed rotational positions, a second detent defining a second rotational position of the plurality of fixed rotational positions, and a third detent defining a third rotational position of the plurality of fixed rotational positions, and wherein the first detent, the second detent, and the third detent are offset from each other around the axis.

17. The system of claim 15, wherein each detent of the plurality of detents is shaped to engage directly with an end surface of the ultrasound probe.

18. The system of claim 17, wherein, while any detent of the plurality of detents is engaged directly with the end surface of the ultrasound probe, a central axis of the ultrasound probe is aligned coaxially with the axis of the probe guide.

19. The system of claim 15, wherein the probe guide further comprises a lower opening shaped to receive a sensor of the ultrasound probe and a protrusion of the outer section that is configured to engage with each detent of the plurality of detents.

20. The system of claim 15, wherein the ultrasound probe is lockable within the probe guide only to any of the plurality of fixed rotational positions defined by the plurality of detents.

* * * * *